United States Patent
Brisben et al.

(10) Patent No.: US 10,849,524 B2
(45) Date of Patent: Dec. 1, 2020

(54) MULTIMODE RATE AND RHYTHM ANALYSIS CALCULATION FOR CARDIAC SIGNAL QUALITY ANALYSIS

(71) Applicant: CARDIAC PACEMAKERS, INC., St. Paul, MN (US)

(72) Inventors: Amy Jean Brisben, St. Paul, MN (US); Krzysztof Z. Siejko, Maple Grove, MN (US); Thomas V. Karathanos, Baltimore, MD (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 285 days.

(21) Appl. No.: 15/889,573

(22) Filed: Feb. 6, 2018

(65) Prior Publication Data
US 2018/0220917 A1    Aug. 9, 2018

Related U.S. Application Data

(60) Provisional application No. 62/455,794, filed on Feb. 7, 2017.

(51) Int. Cl.
| | | |
|---|---|---|
| A61B 5/04 | (2006.01) | |
| A61B 5/0472 | (2006.01) | |
| A61B 5/0452 | (2006.01) | |
| A61B 5/0456 | (2006.01) | |
| A61B 5/00 | (2006.01) | |
| A61B 5/0468 | (2006.01) | |
| A61B 5/046 | (2006.01) | |
| A61N 1/362 | (2006.01) | |
| A61N 1/39 | (2006.01) | |
| A61N 1/05 | (2006.01) | |

(52) U.S. Cl.
CPC ........ *A61B 5/0472* (2013.01); *A61B 5/04014* (2013.01); *A61B 5/0456* (2013.01); *A61B 5/04525* (2013.01); *A61B 5/4836* (2013.01); *A61B 5/7203* (2013.01); *A61B 5/7221* (2013.01); *A61B 5/7285* (2013.01); *A61B 5/046* (2013.01); *A61B 5/0468* (2013.01); *A61N 1/0563* (2013.01); *A61N 1/0587* (2013.01); *A61N 1/3622* (2013.01); *A61N 1/3625* (2013.01); *A61N 1/3904* (2017.08)

(58) Field of Classification Search
CPC ... A61B 5/0472; A61B 5/7221; A61B 5/4836; A61B 5/7203; A61B 5/7285; A61B 5/04014; A61B 5/0456; A61B 5/04525; A61B 5/046; A61B 5/0468; A61N 1/0587; A61N 1/0563; A61N 1/3622; A61N 1/3904; A61N 1/3625
See application file for complete search history.

(56) References Cited

U.S. PATENT DOCUMENTS

| | | |
|---|---|---|
| 6,754,528 B2 | 6/2004 | Bardy et al. |
| 7,248,921 B2 | 7/2007 | Palreddy et al. |
| 7,330,757 B2 | 2/2008 | Ostroff et al. |

(Continued)

*Primary Examiner* — Mallika D Fairchild
(74) *Attorney, Agent, or Firm* — Seager, Tufte & Wickhem LLP

(57) ABSTRACT

Methods and devices adapted for cardiac signal analysis. A method or device has accessible to it more than one approach to cardiac cycle rate analysis and is adapted to monitor sensing signal quality. In response to an apparent reduction in signal quality or other trigger, the method or device checks whether an arrhythmia or an actual drop in signal quality is occurring prior to modifying sensing configurations or parameters.

19 Claims, 15 Drawing Sheets

(56) References Cited

U.S. PATENT DOCUMENTS

| | | |
|---|---|---|
| 7,783,340 B2 | 8/2010 | Sanghera et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,200,341 B2 | 6/2012 | Sanghera et al. |
| 8,494,630 B2 | 7/2013 | Palreddy et al. |
| 8,565,878 B2 | 10/2013 | Allavatam et al. |
| 8,712,523 B2 | 4/2014 | Sanghera et al. |
| 8,825,157 B2 | 9/2014 | Warren et al. |
| 8,827,895 B2 | 9/2014 | Mahajan et al. |
| 8,831,711 B2 | 9/2014 | Freer et al. |
| 9,149,637 B2 | 10/2015 | Warren et al. |
| 9,307,920 B2 | 4/2016 | Mahajan et al. |
| 9,451,892 B2 | 9/2016 | Siejko |
| 9,451,893 B2 | 9/2016 | Siejko et al. |
| 2016/0045132 A1 | 2/2016 | Siejko |
| 2017/0021159 A1 | 1/2017 | Reddy et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0368360 A1 | 12/2017 | Hahn et al. |
| 2018/0036527 A1 | 2/2018 | Reddy et al. |
| 2018/0133462 A1 | 5/2018 | Reddy |
| 2018/0169384 A1 | 6/2018 | Reddy et al. |

MULTIMODE RATE AND RHYTHM ANALYSIS CALCULATION FOR CARDIAC SIGNAL QUALITY ANALYSIS

CROSS REFERENCE TO RELATED APPLICATIONS

The present application claims the benefit of and priority to U.S. Provisional Patent Application Ser. No. 62/455,794, filed on Feb. 7, 2017, the disclosure of which is incorporated herein by reference.

BACKGROUND

Various implantable and wearable cardiac devices are adapted for sensing heart rhythms of a patient. Among implantable systems, earlier versions such as epicardial or transvenous pacemakers or defibrillators included one or more electrodes in or on the heart itself, providing a relatively predictable signal which could vary over time and in response to cardiac conditions. For example, the peak ventricular depolarization signal (the "R-wave") may drop in amplitude during ventricular fibrillation (VF). However, it is desirable to count the R-wave to determine cardiac rate and assess the need for therapy. Algorithmic improvements were introduced as systems became more sophisticated to address such changes.

Newer systems, such as the subcutaneous monitoring device (SMD) and the subcutaneous implantable cardioverter/defibrillator (SICD) do not include electrodes on or in the heart. Further, some proposals for future systems, such as the substernal subcutaneous defibrillator having a lead placed in the mediastinum beneath the sternum, may also lack electrodes in or on the heart. The variability of the cardiac signal with these systems may be greater than that experienced with more traditional systems, and may be affected more greatly by a wider array of inputs. For example, changes in patient posture, activity level, medication and disease state can cause changes in the sensed signal for a given pair of sensing electrodes.

Significant signal changes can lead to undersensing or oversensing, or some of each, and may also hinder the use of some tools, such as R-wave detection and/or morphology matching tools, used to differentiate non-arrhythmic conditions from arrhythmias, or to differentiate atrial from ventricular originating arrhythmias. Resultant overdetection or underdetection can lead to unnecessary therapy and/or impair delivery of life saving therapy.

It has been proposed that sensing reconfiguration may be performed to address signal changes. However, there may be multiple causes for such sensed signal changes. For example, simply assessing amplitude or signal to noise ratio to trigger sensing reconfiguration may cause sensing reconfiguration in response to onset of a dangerous arrhythmia such as VF. New and alternative approaches to identifying signal changes for which sensing reconfiguration is appropriate are desired. It may further be desirable to identify and confirm declines in signal quality before the detected cardiac rate has increased to the point where an arrhythmia episode is declared, in order to prevent the declaration of inappropriate arrhythmias.

OVERVIEW

The present inventors have recognized, among other things, that a problem to be solved is the need to create appropriate triggers for implantable devices to determine when cardiac signal sensing methods are in need of reconfiguration.

A first illustrative non-limiting example takes the form of a method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the method comprising: the operational circuitry monitoring a first sensing configuration to determine whether an arrhythmia is occurring by the use of cardiac cycle detection to detect cardiac cycles and calculate a first cardiac rate; the operational circuitry checking a signal quality of the first sensing configuration and identifying a likely drop in sensing quality of the first sensing configuration; in response to the likely drop in sensing quality of the first sensing configuration, the operational circuitry performing a rate analysis of the patient's cardiac signal using a method other than cardiac cycle detection to generate a second cardiac rate and a confidence; and either: the operational circuitry determining that an arrhythmia is occurring, based on at least the confidence of the rate analysis; or the operational circuitry determining a drop in signal quality is occurring and the first sensing configuration should be changed.

A second illustrative non-limiting example takes the form of a method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the method comprising: the operational circuitry monitoring a first sensing configuration to determine whether an arrhythmia is occurring by the use of cardiac cycle detection to detect cardiac cycles and calculate a first cardiac rate; the operational circuitry checking a signal quality of the first sensing configuration and identifying a likely drop in sensing quality of the first sensing configuration; in response to the likely drop in sensing configuration, the operational circuitry performing a rate analysis of the patient's heart using a method other than cardiac cycle detection to yield a second cardiac rate; the operational circuitry analyzing the second cardiac rate and determining that the second cardiac rate is in an arrhythmia zone; and the operational circuitry determining that an arrhythmia is occurring, rather than a drop in signal quality.

A third illustrative non-limiting example takes the form of a method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the method comprising: monitoring a first sensing configuration to determine whether an arrhythmia is occurring by the use of cardiac cycle detection to detect cardiac cycles and calculate a first cardiac rate; checking a signal quality of the first sensing configuration and identifying a likely drop in sensing quality of the first sensing configuration; in response to the likely drop in sensing quality of the first sensing configuration, attempting a rate analysis of the patient's cardiac rhythm using an autocorrelation method not reliant on cardiac cycle detection; finding that the rate analysis using the autocorrelation method fails to yield a reliable second cardiac rate; and in response to finding that that the rate analysis using the autocorrelation method fails to yield a reliable second cardiac rate, concluding that a supraventricular arrhythmia is occurring and no sensing configuration change is needed due to drop in sensing quality.

Additionally or alternatively to any of the first to third non-limiting examples, the step of determining that an arrhythmia is occurring comprises identifying a type of arrhythmia using at least the confidence and the second cardiac rate.

Additionally or alternatively to any of the first to third non-limiting examples, the step of checking a signal quality of the first sensing configuration is performed by assessing signal quality of the first sensing configuration in an ongoing manner with each detected cardiac cycle.

Additionally or alternatively to any of the first to third non-limiting examples, the step of checking a signal quality of the first sensing configuration is performed by assessing signal quality of the first sensing configuration at a predefined interval.

Additionally or alternatively to any of the first to third non-limiting examples, the step of checking a signal quality of the first sensing configuration is performed in response to determining that the first cardiac rate has exceeded a threshold.

Additionally or alternatively to any of the first to third non-limiting examples, the step of performing a rate analysis of the patient's cardiac signal using a method other than cardiac cycle detection comprises: selecting a first portion the patient's cardiac signal to compare to a second portion of the patient's cardiac signal; repeatedly comparing the first portion of the patient's cardiac signal at a plurality of alignments defined by a plurality of corresponding lag depths to yield a plurality of comparison scores; and selecting one or more peak comparison scores and using a lag depth corresponding to the selected peak comparison scores to calculate the second cardiac rate.

Additionally or alternatively each of the first portion and second portion of the cardiac signal are obtained using the first sensing configuration.

Additionally or alternatively the second portion of the cardiac signal at least partly overlaps the first portion of the cardiac signal; the first portion of the cardiac signal has a duration in the range of about 500 milliseconds to 2000 milliseconds; and the second portion of the cardiac signal has a duration greater than that of the first portion of the cardiac signal.

Additionally or alternatively, the step of selecting one or more peak comparison scores comprises defining a zero lag depth point, identifying a first peak comparison score having a first lag depth relative to the zero lag depth point, and determining that a second peak comparison score appears at a second lag depth relative to the zero lag depth point which is approximately an integer multiple of the first lag depth.

Additionally or alternatively to any of the first to third non-limiting examples, the operational circuitry may compare the first cardiac rate to the second cardiac rate; wherein the step of determining that an arrhythmia is occurring, rather than a drop in signal quality, based on a result of the rate analysis is performed in response to the operational circuitry finding that the second cardiac rate equals or exceeds the first cardiac rate; and wherein the step of determining that the first sensing configuration should be changed is performed in response to the operational circuitry finding that the second cardiac rate is less than the first cardiac rate and below a threshold for declaration of tachyarrhythmia.

Additionally or alternatively to any of the first to third non-limiting examples, further comprising the operational circuitry comparing the first cardiac rate to the second cardiac rate and: the step of determining that an arrhythmia is occurring, rather than a drop in signal quality, based on a result of the rate analysis is performed in response to finding that the second cardiac rate equals the first cardiac rate within predetermined bounds; and the step of determining that the first sensing configuration should be changed is performed in response to finding that the second cardiac rate is different from the first cardiac rate outside the predetermined bounds.

Additionally or alternatively to the third illustrative non-limiting example, the autocorrelation method comprises: selecting a first portion the patient's cardiac signal to compare to a second portion of the patient's cardiac signal; repeatedly comparing the first portion of the patient's cardiac signal at a plurality of alignments defined by a plurality of corresponding lag depths to yield a plurality of comparison scores; identifying one or more peak comparison scores each having a corresponding first lag depth; and observing whether, for each of the selected one or more first peak comparison scores, a second peak comparison score appears at a second lag depth which is an integer multiple of the first lag depth; further wherein finding that the rate analysis using the autocorrelation method fails to yield a reliable second cardiac rate comprises determining that no such second peak comparison score appears for each one or more first peak comparison scores selected.

Additionally or alternatively to the third illustrative non-limiting example, the autocorrelation method comprises: selecting a first portion the patient's cardiac signal to compare to a second portion of the patient's cardiac signal; repeatedly comparing the first portion of the patient's cardiac signal at a plurality of alignments defined by a plurality of corresponding lag depths to yield a plurality of comparison scores; and comparing the plurality of comparison scores to a comparison score threshold; and further wherein finding that the rate analysis using the autocorrelation method fails to yield a reliable second cardiac rate comprises determining that none of the comparison scores exceeds the comparison score threshold.

A fourth illustrative non-limiting example takes the form of a method of cardiac signal discrimination in an cardiac system comprising an implantable device and an external device, the implantable device and external device configured to communicate with one another, the implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the method comprising: the implantable device monitoring a first sensing configuration to determine whether an arrhythmia is occurring by the use of cardiac cycle detection generating a plurality of cardiac cycle detections and a first cardiac rate; the implantable device checking a signal quality of the first sensing configuration and identifying a likely drop in sensing quality of the first sensing configuration; the implantable device communicating to an external device in response to the likely drop in sensing quality, including at least a block of cardiac signal data; the external device, or a device operatively linked to the external device by a communications or network interface, performing a rate analysis of the patient's cardiac signal using a method other than cardiac cycle detection applied to the communicated block of cardiac signal data to yield a second cardiac rate and a confidence; and either: the external device, or the device operatively linked to the external device, determining that an arrhythmia is occurring, rather than a drop in signal quality, based on the second cardiac rate and confidence and, if so, generating an alert to at least one of the patient or a physician for the patient; or the external device, or the device operatively linked to the external device, determining that the first sensing configuration should be changed, and either communicating to the implantable device indicating the first sensing configuration should be changed, or generating a physician alert indicating the first sensing configuration should be changed.

A fifth illustrative, non-limiting example takes the form of a method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the method comprising: monitoring a first sensing configuration to determine whether an arrhythmia is occurring by the use of cardiac cycle detection to detect cardiac cycles and calculating a first cardiac rate; checking a signal quality of the first sensing configuration and identifying a likely drop in sensing quality of the first sensing configuration; in response to the likely drop in sensing quality of the first sensing configuration, performing a rate analysis of the patient's cardiac signal using a method other than cardiac cycle detection to generate a second cardiac rate and a confidence; analyzing the confidence to eliminate a possibility of a supraventricular arrhythmia; determining that a supraventricular arrhythmia is unlikely by observing a high confidence in the second cardiac rate; comparing the first cardiac rate to the second cardiac rate and finding a mismatch; in response to the combination of a finding that supraventricular arrhythmia is unlikely and mismatch of the first and second rates, performing reconfiguration of the first sensing configuration.

A sixth illustrative non-limiting example takes the form of an implantable medical device comprising a plurality of electrodes adapted for sensing cardiac signals of a patient and operational circuitry coupled to the plurality of electrodes such that a plurality of sensing configurations among the sensing electrodes and one or more circuits of the operational circuitry are available to the operational circuitry, the operational circuitry configured to perform as the implantable medical device in a method as in any of the first to fifth illustrative, non-limiting examples, or any variant thereof.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
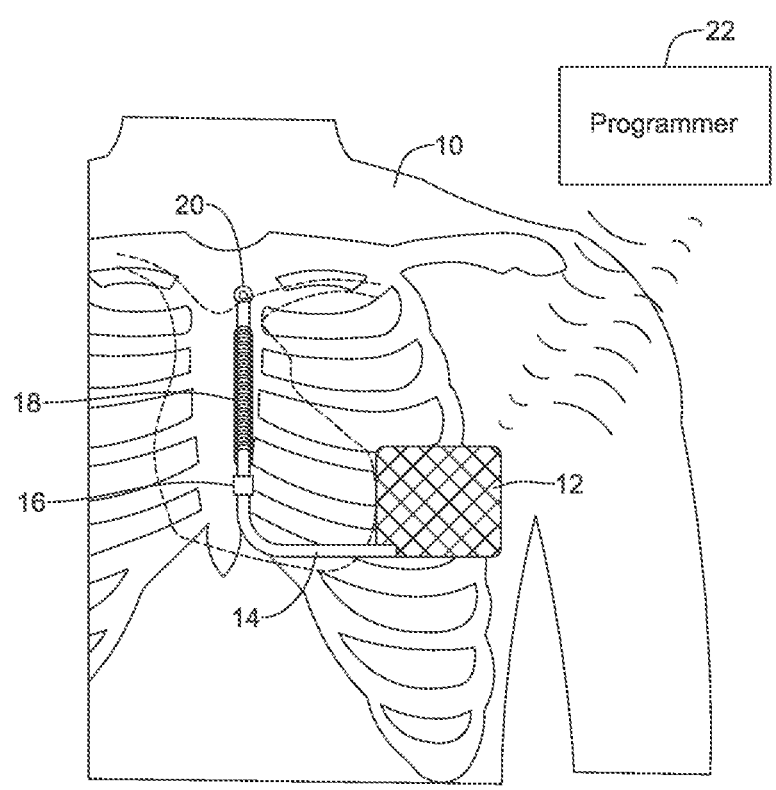
FIG. 1 shows an illustrative implantable medical device system.

FIG. 1 shows illustrative implantable medical device system. In some examples, the system of FIG. 1 may take a form similar to the S-ICD System™ from Cameron Health, Inc., and Boston Scientific Corporation. In such an example, the system would be implanted in a patient 10 with a canister 12 in the left axilla at about the level of the cardiac apex. A lead 14 is placed subcutaneously, beneath the skin and over the ribcage of the patient, with a first portion extending along the inframammary crease from the canister 12 to approximately the xiphoid, and then superiorly parallel to and about 1-2 cm to the left of the sternum. A proximal sense electrode 16, shocking coil electrode 18, and distal tip sense electrode 20 are provided along the parasternal portion of the lead 14.

In the S-ICD System™, the entire system is implanted outside of the ribcage of the patient. In other examples, the distal portion of the lead may be implanted beneath the sternum in a "substernal" position, with one or more of the electrodes 16, 18, 20 generally in the mediastinum. For a substernal position, the device may be extravascular and located beneath the ribs or sternum without attachment to the heart and/or pericardium. Some examples of such a substernal placement are described in U.S. patent application Ser. No. 15/208,682, titled SUBSTERNAL PLACEMENT OF A PACING OR DEFIBRILLATING ELECTRODE, the disclosure of which is incorporated herein by reference.

The implantable system may also be placed as shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference, in which the lead 14 may be inserted into an internal thoracic vein, for example, and placed in the internal thoracic vein at a desired location relative to the heart. The lead 14 may be implanted with one or more electrodes 16, 18, 20 in an internal thoracic vein itself, or, the mediastinum may be accessed from an internal thoracic vein as discussed in U.S. patent application Ser. No. 15/814,990, titled TRANSVENOUS MEDIASTINUM ACCESS FOR THE PLACEMENT OF CARDIAC PACING AND DEFIBRILLATION ELECTRODES, the disclosure of which is incorporated herein by reference. Still further, one or more intercostal veins may be used for lead implant, as discussed in U.S. patent application Ser. No. 15/846,081, titled IMPLANTATION OF AN ACTIVE MEDICAL DEVICE USING THE INTERCOSTAL VEIN, the disclosure of which is also incorporated herein by reference.

In other examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history, and potential problems to the user/medical practitioner, and may also allow for updating of programming in the canister 12.

Specific to the device shown in FIG. 1, unlike prior art defibrillators and pacemakers that include electrodes in or on the heart, the device (whether subcutaneous-only, substernal, or using the internal thoracic vein, mediastinum and/or intercostal vein(s)) uses only far-field electrodes located away from the heart for detecting cardiac activity. This can make counting cardiac cycles more difficult than with systems having an electrode in or on the heart, as the source of the detected signal may be harder to distinguish. For example, while a ventricular depolarization detected with a transvenous, intracardiac electrode may be quite sharp and narrow in width, the same signal will be wider and less sharp when detected in the far field.

A system as shown in FIG. 1 provides a number of available sensing vectors that can be used to detect cardiac activity. For example, signals may be sensed using electrode 20 paired with any of electrodes 16, 18 or the active canister 12. The cardiac signal will vary among these vectors, as illustrated in U.S. Pat. No. 8,825,157, titled VECTOR SWITCHING IN AN IMPLANTABLE CARDIAC STIMULUS SYSTEM, the disclosure of which is incorporated herein by reference.

Vector selection may be used to optimize sensing the sensing configuration to a particular patient using, for example, one or more of signal to noise ratio, R-wave amplitude, and/or variations of such factors as measured over time. Illustrative examples of vector selection may be found, for example, in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, the disclosure of which is incorporated herein by reference. For example, a number of cardiac cycles may be detected and various metrics including R-wave amplitude, signal-to-noise ratio, or any other desired metric, may be generated for one or several available sensing vectors, and the "best scoring" of such vectors may be selected as one or more default sensing vectors. By "best scoring", this may indicate the vector with some desired combination of R-wave amplitude and signal-to-noise ratio and/or consistency of such factors over time, for example. Various illustrative calculations are noted in the U.S. Pat. No. 7,783,340 patent that may be used.

In addition, the signal detected by a given pair or group of implanted electrodes may vary in relation to patient activity, posture, or other factors. The sensing configuration may be optimized further by performing an analysis across multiple patient postures. Some examples are shown in U.S. Pat. No. 8,200,341, titled SENSING VECTOR SELECTION IN A CARDIAC STIMULUS DEVICE WITH POSTURAL ASSESSMENT, the disclosure of which is incorporated herein by reference.

To further enhance operations, data from multiple vectors may be combined together by, for example, combining signals of multiple vectors together and performing analysis thereof, or by analyzing multiple channels of data and combining the resultant data, such as indications of cardiac cycle detections, noise, or other features, together. See, for example, U.S. patent application Ser. No. 15/297,588, titled MULTI-VECTOR SENSING IN CARDIAC DEVICES WITH SIGNAL COMBINATIONS, and U.S. Ser. No. 15/297,605, titled MULTI-VECTOR SENSING IN CARDIAC DEVICES WITH DETECTION COMBINATIONS, the disclosures of which are incorporated herein by reference. In addition, the signals in multiple sensing vectors may be monitored over time for changes in signal quality, as discussed, for example, in U.S. patent application Ser. No. 15/297,568, titled SIGNAL QUALITY MONITORING FOR MULTIPLE SENSE VECTORS IN CARDIAC DEVICES, the disclosure of which is incorporated herein by reference.

Figure 8:
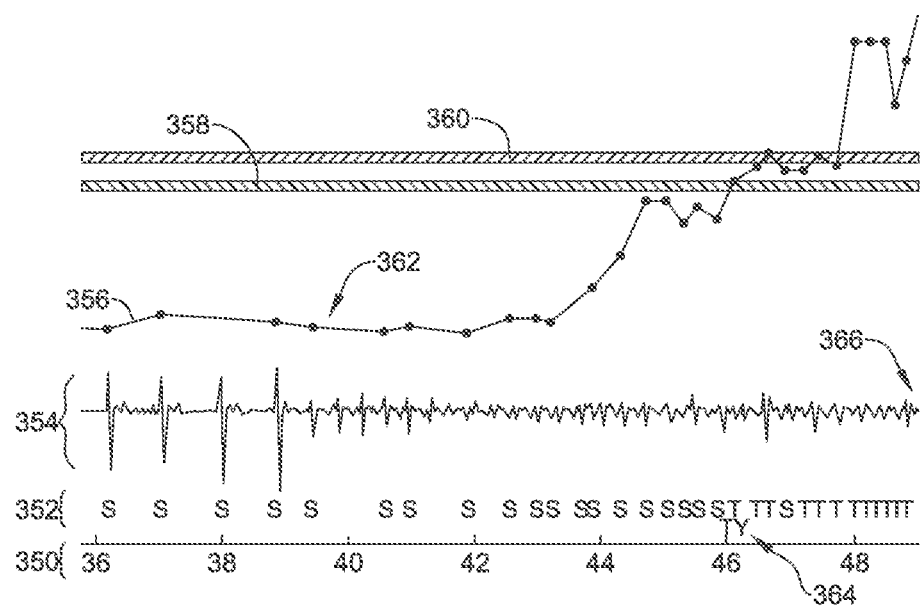
FIGS. 8-9 show cardiac cycle analyses comparing poor signal quality (FIG. 8) to arrhythmia onset (FIG. 9)

The concept of monitoring for signal quality changes and changing sensing configurations can be quite helpful. However, FIGS. 8 and 9 demonstrate a difficulty that can arise. Referring to FIG. 8, a timeline is provided at 350 in seconds, with markers shown at 352 to correspond to a cardiac device's sensing outputs during analysis of the cardiac signal shown at 354. A line at 356 reflects the calculated rate of cardiac cycles, with rate thresholds for ventricular tachycardia (VT) shown at 358 and ventricular fibrillation (VF) shown at 360. In the example, the signal 354 changes at about 39 seconds, as indicated by the arrow at 362. Prominent R-waves reduce in amplitude relative to the rest of the signal, and continue to shrink to lower levels by about 42 seconds. The source of such a change may be, for example, the patient changing postures and starting a physical activity as by standing and beginning to walk or run. In any event, the true rate of cardiac cycles has increased while the amplitude of the signal and therefore the sensing quality has dropped.

Still referring to FIG. 8, at about 44 seconds, the detected rate 356 increases greatly and by 46 seconds, a tachycardia is declared as indicated at 364. Due to the poor quality of the signal, the cardiac cycles begin to be oversensed between 46 and 48 seconds, such that the rate 356 exceeds the VF line 360, and the device begins charging for delivery of a defibrillation shock at about 49 seconds, as indicated by the arrow at 366. While the actual rate of cardiac cycles in the example remains in the range of about 160-180 beats per minute (BPM), the drop in amplitude causes oversensing and drives the detected cardiac cycle rate over 200 BPM, potentially leading to an inappropriate shock for exercised induced sinus tachycardia. It is not, however, a simple expedient to determine that the signal amplitude dropped and a different sense vector should be used, as shown by FIG. 9.

Figure 9:
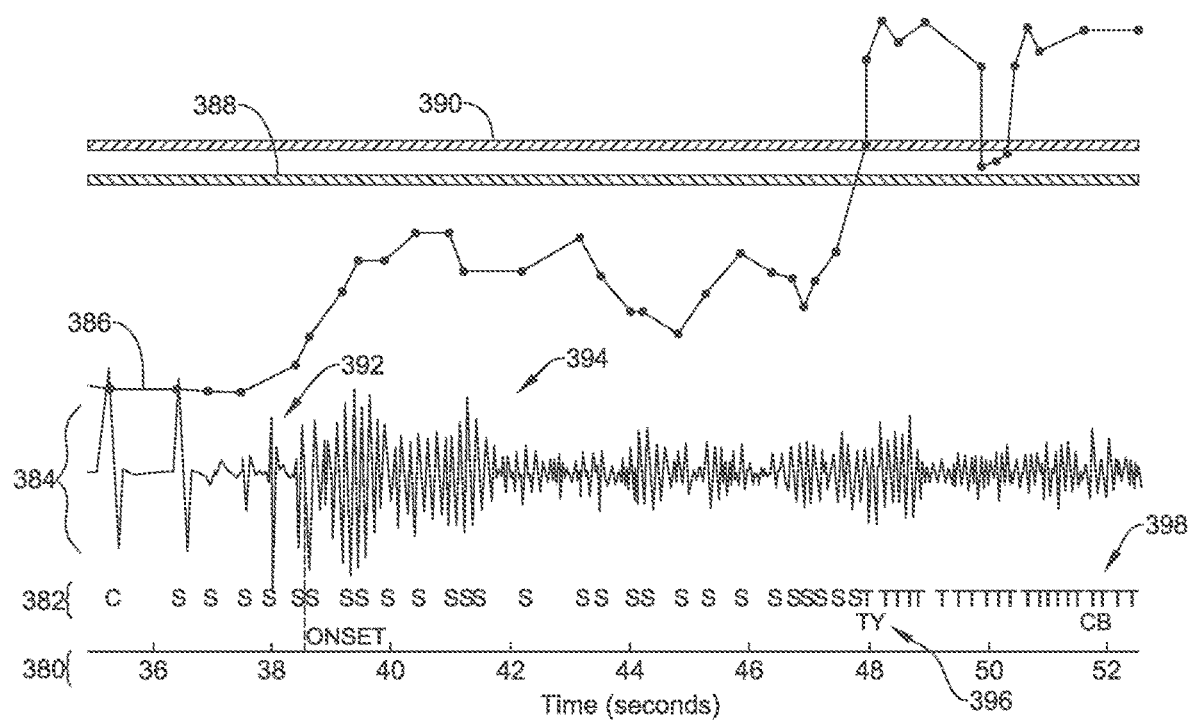

FIG. 9 is similar in structure to FIG. 8, but the cardiac signal is different. A timeline is provided at 380, with markers shown at 382 for a signal 384. The calculated cardiac cycle rate is shown at 386, relative to the VT threshold 388 and VF threshold 390. Here, an arrhythmia onset occurs at 392, with the regular amplitudes of R-waves and large signal to noise ratio preceding 38 seconds replaced with a far more variable signal. A ventricular fibrillation is shown, with some initial Torsades signal illustrated by the periodic variation of the fibrillation peak amplitudes at 394, and then drop to a lower amplitude signal. Due to the amplitude variations, the system does not immediately identify the arrhythmia, with some undersensing illustrated until the high rate is detected at about 47 seconds, leading to tachycardia declaration at 396 and charge begin at 398 in preparation for a defibrillation shock.

Ultimately, the problem shown in FIGS. 8-9 is that it can be difficult to set rules that distinguish a reduction in sensed signal quality from onset of an arrhythmia. The characteristics of fibrillation may include poor signal-to-noise ratio, variable peak amplitude, and drop in overall signal strength; such features are largely the same as the features of onset of a poor signal. New and alternative approaches that can distinguish poor sensing from arrhythmia onset are desired.

It is a goal of some embodiments of the present invention to introduce an early intervention that can identify and confirm declines in signal quality before rate increases to the point where an episode is declared, preventing inappropriate declaration of arrhythmia and/or inappropriate therapy delivery. For example, the drop in signal amplitude at about 39 seconds could be sensed/detected and used to trigger analysis, and this may be repeated again later in the strip with the tachy declaration at 364, each of which occur prior to the initiation of charging 366 of FIG. 8.

Figure 2:
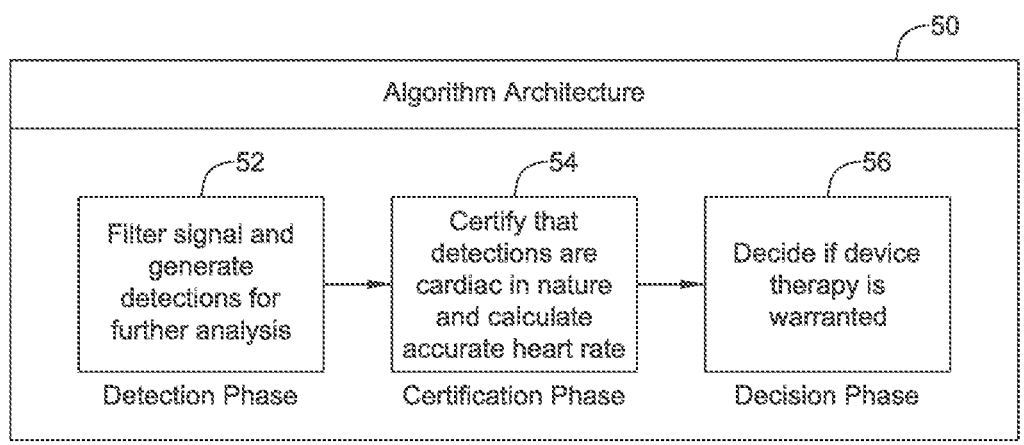
FIG. 2 illustrates a cardiac signal analysis algorithm.

FIG. 2 shows an illustrative cardiac signal analysis architecture. The architecture 50 includes a detection phase 52 in which the input signal is filtered and cardiac cycle detections are generated for further analysis. Filtering may include both analog domain and digital domain filtering. For example a bandpass filter may be applied in the analog domain to remove DC and high frequency content, for example, using ranges of 3 to 40 Hz. Additional band stop filtering may be applied in the digital domain to remove 50/60 Hz line noise, and additional band-pass filtering may be performed to obtain desired cardiac signal bands in the range of between about 3-10 Hz and about 30-40 Hz. Other filter architectures may be used. Some examples related to filtering may be found in U.S. patent application Ser. No. 15/362,862, titled AUTOMATIC DETERMINATION AND SELECTION OF FILTERING IN A CARDIAC RHYTHM MANAGEMENT DEVICE, the disclosure of which is incorporated herein by reference.

Figure 3:
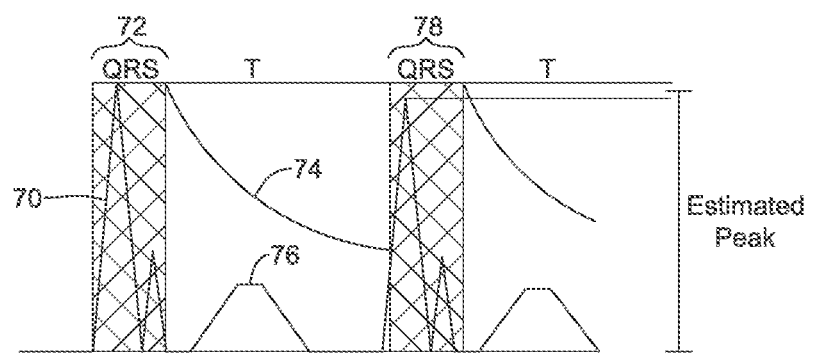
FIG. 3 illustrates an approach to cardiac cycle detection.

FIG. 3 shows an example of cycle detection usable in block 52, and is further discussed below. Some examples of cardiac cycle detection may be found, for example, in U.S. Pat. No. 8,565,878, titled ACCURATE CARDIAC EVENT DETECTION IN AN IMPLANTABLE CARDIAC STIMULUS DEVICE, the disclosure of which is incorporated herein by reference.

Detections generated by detection phase 52 pass to certification phase 54. Certification phase 54 may be designed to remove or correct for detections that are non-cardiac in nature, passing only those that are cardiac and not double detected for use in rate calculation. Certification may include, for example, identification and removal of cycle detections caused by noise, saturation, or wandering baseline as discussed, among other examples, in U.S. Pat. No. 7,248,921, titled METHODS AND DEVICES FOR PERFORMING CARDIAC WAVEFORM APPRAISAL, U.S. Pat. No. 8,712,523, titled IMPLANTABLE DEFIBRILLATOR SYSTEMS AND METHODS WITH MITIGATIONS FOR SATURATION AVOIDANCE AND ACCOMMODATION, and U.S. Pat. No. 8,831,711, titled IMPLANTABLE CARDIAC SYSTEMS WITH BASELINE CORRECTION IN RESPONSE TO NOISE DETECTION, the disclosures of which are incorporated herein by reference.

Certification phase 54 may also remove overdetections using, for example, methods and devices shown in U.S. Pat. Nos. 8,160,686 and/or 8,160,687, both titled METHODS AND DEVICES FOR ACCURATELY CLASSIFYING CARDIAC ACTIVITY, the disclosures of which are incorporated herein by reference.

A cardiac cycle rate may be calculated using by measuring the intervals between individual detections that have been certified as cardiac and correct. A set of 1 to 8 intervals may be averaged to obtain an average cycle length, which can then be mathematically converted to a rate. For example, a 4RR average may be the average of four intervals between certified R-wave detections, and may be used to determine cardiac rate, where a 4RR average of 500 milliseconds would equal to 120 BPM.

In some examples, the signal quality analysis performed may precede the decision phase 56 to prevent inappropriate declaration of episodes. If signal quality changes are identified independent of arrhythmia, a patient or physician may be notified of such occurrences in order to encourage review of the patient's condition and any relevant device configuration or setting, or by reviewing the patient's device itself to ensure proper placement thereof and that the sensing lead placement is and remains correct.

A closed-loop system may automatically and independently perform reconfiguration of itself under appropriate circumstances. For example, in response to a finding that the patient has experienced a signal quality drop, an implanted device may wait for a time period when the patient is at rest before performing signal reanalysis. On the other hand, a device may use closed loop adjustment automatically and immediately, since the poor sensing quality identified may be relevant only when the patient is, for example, in a certain posture or performing a certain activity, such that waiting for the patient to be at rest would miss the opportunity for optimization. In some examples, there may be a tiered closed loop response where, in a first tier, the device waits to reconfigure sensing until the patient is at rest, and in a second tier, the device does not wait if the issue arises again.

Decision phase 56 operates to decide whether device therapy is warranted, for those devices that can deliver therapy. Decision phase 56 may rely on detected cardiac rate alone, or a combination of cardiac rate and other factors such as cardiac signal shape using, for example, R-waves, QRS complexes, or other parts of the cardiac electrical signal, or non-cardiac electrical signals such as heart sounds, blood pressure measurements, patient activity or posture, etc. Some examples of decision phase may have a tiered approach in which, if the cardiac rate is below a tachycardia threshold, therapy is withheld, while if cardiac rate is above a ventricular fibrillation threshold, therapy delivery is considered necessary, while rates between the tachycardia threshold and ventricular fibrillation threshold warrant further analysis using, for example, static or dynamic template matching, width, or other factors.

A common approach, referenced below in several places, is for the decision phase to itself have two parts. A first decision is made as to whether a particular iteration of the architecture's operation indicates a treatable condition. This decision is tied to each cardiac cycle detection, or to only those detections that pass certification phase 54. A set of first decisions is retained in a counting filter, for example, an X/Y filter or a number-of-intervals-to-detect (NID) filter. As used herein, the phase "X/Y filter" should be understood to include both NID and X/Y filter approaches.

An X/Y filter, for example, tracks how many iterations of the decision phase 56 come to the conclusion that a treatable condition may exists (X) of a preceding set of iterations (Y). Typical thresholds for X/Y may be 8/12, 18/24, 30/40, for example. Various analysis and manipulations may be used for an X/Y filter. For example, in an analysis using a 4 RR average, explained above, once the 4 RR average exceeds a fast rate threshold, the X/Y filter may go from 0/Y to 1/Y, in a conservative method. Alternatively, for a 4RR average, the first time the rate goes above the fast rate threshold, the X/Y filter may jump to 4/Y, in an aggressive method, where the use of the larger seeding is based on the knowledge that it took several fast cardiac cycle detections to get the 4 RR average over the threshold. Other manipulations may, for example, reduce the X/Y filter by steps of 1 to 3 if a cardiac cycle detection from the detection phase 52 fails at certification 54 due to noise and/or overdetection analysis. As the X/Y filter operates, new analysis outcomes go into and out of the filter data in a first in-first out manner.

The second stage or tier of analysis in the decision phase 56 may look at the overall rhythm using the X/Y filter output. For example, a threshold for treatable condition declaration may take place at an X/Y filter level of 18/24. Some examples may further apply rules for persistence, for example as described in U.S. Pat. No. 8,160,697, titled METHOD FOR ADAPTING CHARGE INITIATION FOR AN IMPLANTABLE CARDIOVERTER-DEFIBRILLATOR, the disclosure of which is incorporated herein by reference, to require that the treatable overall rhythm remain in place for one or several consecutive cycle detections.

Other examples for decision phase 56 methods/devices may be bound in U.S. Pat. No. 7,330,757, titled METHOD FOR DISCRIMINATING BETWEEN VENTRICULAR AND SUPRAVENTRICULAR ARRHYTHMIAS, in which both rate and morphology analysis may be used in a tiered fashion. For example, a ventricular tachycardia (VT) rate zone may be defined as well as a ventricular fibrillation (VF) rate zone, with the boundary for VF at a higher rate than VT. When the calculated rate is in the VT zone, morphology analysis, such as the matching of detected cardiac cycles to a template, or to each other, or assessment of the individual cycles using a metric such as width, is applied. In an example, VT zone cycles having poor template correlation relative to a normal sinus rhythm (NSR) template, and which are wide or are inconsistent in shape, may be deemed treatable; those which match the NSR and/or which are narrow and match one another may be deemed non-treatable. Continuing the example, when the rate is found to be in the VF zone, each detected cycle associated with such a rate would be found treatable.

Additional analysis may be performed using methods shown in U.S. Pat. No. 9,149,637, titled ADAPTIVE CONFIRMATION OF TREATABLE ARRHYTHMIA IN IMPLANTABLE CARDIAC STIMULUS DEVICES, the disclosures of which are incorporated herein by reference. These methods may manipulate the thresholds used in the decision phase upon completion of preparation for therapy delivery such as, for example, in a defibrillator system where several seconds may pass while a therapy delivery energy is generated by charging one or several capacitors to desired voltage/energy level.

If all the applicable rules are met, then therapy delivery will be deemed appropriate. Therapy delivery may include anti-tachycardia pacing, defibrillation or cardioversion therapy, a command to a separate device to deliver therapy, or delivery of a therapeutic substance, in various examples. For high power therapy such as defibrillation, there may be a need to continue operating the architecture 50 while therapy preparations are made, such as charging a high-power capacitor; the noted U.S. Pat. Nos. 8,160,697 and 9,149,637 describe certain illustrative methods. For non-therapy devices, such as monitoring systems, the outcomes at decision phase 56 may be used to activate data recording or storage for later retrieval, or to activate a patient alarm or alert, or to telemeter data related to unusual or elevated rate conditions to a second device/system.

FIG. 3 shows use of a detection profile to detect cardiac cycles using the R-wave as a detection target. A cardiac electrical signal is shown at 70; the example is based on a subcutaneous electrocardiogram, though signal 70 could as well be a cutaneously captured signal instead, or a signal from a substernal, mediastinum electrode or electrode pair, or from electrodes in an internal thoracic vein or intercostal vein.

A first cardiac cycle detection is shown at 72, corresponding to the QRS complex of a patient's cardiac cycle. The cross hatched region is a "refractory" period in which no further detected cycles are declared to allow the QRS complex to finish prior to enabling new detections to occur. A time decaying detection threshold is depicted at 74, and starts at a level defined by prior detected cycle amplitude(s). The threshold 74 decays over time until the cardiac signal 70 crosses the detection threshold 74, generating another cardiac cycle detection at 78, again a QRS complex. The overall shape of the threshold 74 may be defined according to a "detection profile", as further detailed throughout U.S. Pat. No. 8,565,878, for example. Signal 70 has a relatively small T-wave 76, at least in proportion to the QRS complex height 72, 78, making accurate detection of cardiac cycles relatively simple.

Even with various mitigations in place, overdetection of cardiac cycles based on oversensing of the cardiac signal (or non-cardiac signals) occurs in implantable and wearable therapy systems, causing unnecessary and inappropriate charging and/or therapy delivery. In monitoring systems, overdetection/oversensing can create unnecessary alerts and may fill data recorders with unhelpful data demonstrating malsensing rather than sought after intermittent cardiac impairments. For these and other reasons, additional efforts have been made to identify cardiac rate by other analyses.

Figure 4:
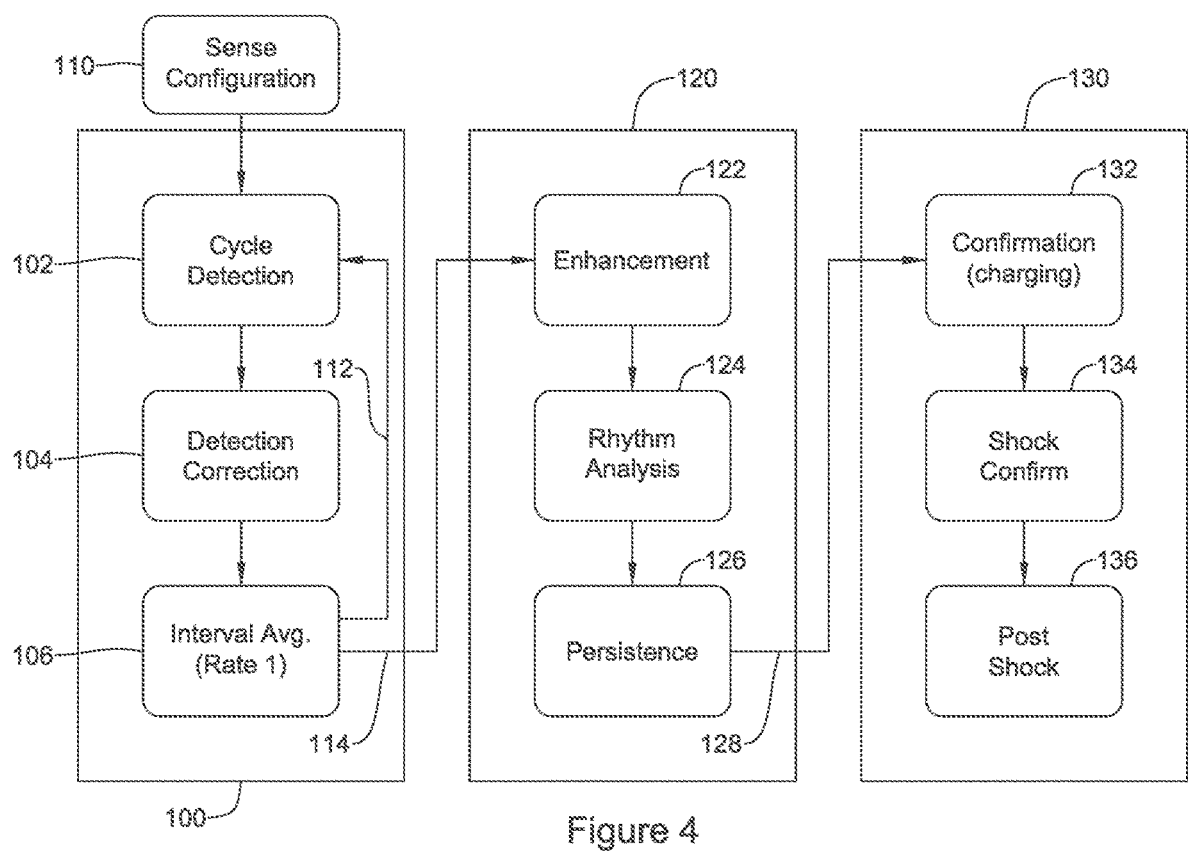
FIG. 4 shows a more detailed cardiac signal analysis algorithm.

FIG. 4 shows a more detailed cardiac signal analysis algorithm. The operation is iterative and begins with cardiac cycle detection 102, in which a method as in FIG. 3 may be performed to detect cardiac cycles using, for example, the R-wave or QRS complex, or any other repeatably detectable part of the cardiac cycle. Cardiac cycle detections or "raw detections" may be analyzed and corrected, as indicated at 104, to eliminate noise and/or overdetection. An interval average is then generated as indicated at 106 to yield a cardiac rate, which is referred to as "Rate 1" or a first cardiac rate in several examples. Blocks 102, 104, 106 are part of the basic cycle 100 of the analysis. Cardiac cycle detection 102 relies in part on the use of a sensing configuration 110. The sensing configuration 110 may include, for example, definition of one or more sense vectors to be used and associated characteristics such as filtering and/or amplification characteristics to be used. A sensing configuration 110 may also comprise additional features such as stored templates corresponding to one or more known cardiac rhythm states, such as a normal sinus rhythm template, and/or a template associated with an exercise-induced sinus tachycardia or a known, pace terminable monomorphic ventricular tachycardia.

In some examples, cycle detection 102 may additionally include sensing for particular features such as the R-wave and P-wave, differentiating ventricular and atrial depolarizations, as discussed in U.S. PG Patent Pub. No. 2017/0368360, titled CARDIAC THERAPY SYSTEM USING SUBCUTANEOUSLY SENSED P-WAVES FOR RESYNCHRONIZATION PACING MANAGEMENT. Characteristics useful for P-wave detection may be integrated in the sense configuration 110 as well.

The basic cycle 100 may be used when the detected rate is relatively low. If the rate increases above a threshold in the range of about 100 to 200 BPM, an enhanced analysis 120 may be applied. The threshold for additional analysis may be user selectable or may be a default of the system; for example, a VT threshold may be user selected to account for patient characteristics to avoid over-triggering enhanced analysis.

The enhanced analysis 120 may include analysis of characteristics of one or plural detected events alone or in conjunction with one another in an enhancement analysis 122. The aim may be to differentiate supraventricular tachycardias (such as atrial flutter or fibrillation, as well as sinus tachycardia) from ventricular originating arrhythmias. For example, features such as interval stability, (sudden) onset, QRS width, morphology comparisons (matching to a template or to adjacent events), signal variability, or other features, may be assessed. Some example enhancements are discussed in U.S. Pat. No. 7,330,757, titled METHOD FOR DISCRIMINATING BETWEEN VENTRICULAR AND SUPRAVENTRICULAR ARRHYTHMIAS, and/or U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR, the disclosure of which are incorporated herein by reference. Enhancement analysis 122 may vary depending on the rhythm sought; for example, markers for an SVT may be analyzed (interval stability for example) in a first tier and markers for a monomorphic VT (short intervals with consistent wide morphology) in a second tier, as one tier may drive a different therapy determination and/or inhibit operation of another.

Next, the illustrative method turns to a rhythm analysis 124. Rhythm analysis 124 may include consideration of a plurality of analysis outcomes from the enhancement operator 122 and may use, for example, an X/Y filter as discussed above. A persistence factor 126 may be applied as well to ensure that a treatable rhythm persists for at least some minimum duration or quantity of analytical outcomes. If rhythm analysis 124 and/or persistence 126 finds conditions non-treatable, the method can return to block 102. If rhythm analysis 124 and persistent 126 agree that the cardiac activity detected is treatable, the method can proceed 128 to a therapy block 130.

Therapy bock 130 includes a first confirmatory block 132 that checks on whether the most recently received data continues to support shock delivery and, if so, charging of the device capacitor for high energy defibrillation therapy (high energy may mean, for example, on the order of 1-80 Joules, depending on the specific configuration of an implantable device, with 1-40 Joules likely for a transvenous system, up to 80 Joules, or more, for a subcutaneous-only system, and intermediate levels of, for example, up to 50 or 60 Joules for substernal and/or internal thoracic vein implant locations). Once charging is initiated, the system continues to operate using at least portions of the basic analysis 100 and enhanced analysis 120 to continue monitoring cardiac activity. If the detected arrhythmia ceases, then charging may be terminated prior to completion. Once charging is completed, therapy block will perform a shock confirmation 134 to again confirm therapy is needed. Shock confirmation may optionally include additional analysis such as disclosed in U.S. Pat. No. 9,149,637, titled ADAPTIVE CONFIRMATION OF TREATABLE ARRHYTHMIA IN IMPLANTABLE CARDIAC STIMULUS DEVICES, the disclosure of which is incorporated herein by reference. Other shock confirmation may be used as desired.

Once shock confirmation 134 is satisfied, a high energy shock can be delivered to defibrillate the patient. In some examples, tiered therapy may be used including delivery of anti-tachycardia pacing. For example, the enhancement block 122 may determine that a pace-terminable ventricular tachyarrhythmia is occurring, and ATP can be delivered prior to charging beginning in block 130, or while charging is ongoing, as desired. Following shock delivery, a post shock operation 136 can take place including, for example, delivery of post-shock anti-asystole or anti-bradycardia pacing, as well as clearing or manipulating one or more counters or settings to facilitate sensing of the cardiac signal after therapy delivery. For example, U.S. Pat. No. 8,494,630, titled DATA MANIPULATION FOLLOWING DELIVERY OF A CARDIAC STIMULUS IN AN IMPLANTABLE CARDIAC STIMULUS DEVICE, discusses optional post-therapy methods that may be included in block 136.

Figure 5:
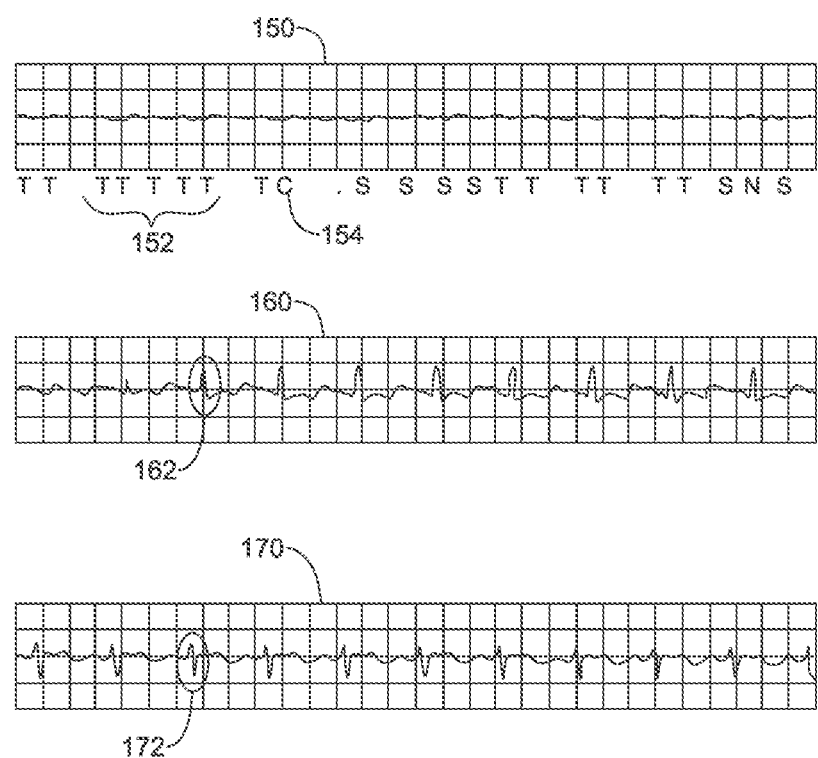
FIG. 5 illustrates graphically different sense vectors in relation to a cardiac signal with notations for cardiac cycle detection.

FIG. 5 illustrates graphically signals received along different sense vectors in relation to a cardiac signal with notations for cardiac cycle detection. As noted above, an element of a sensing configuration may include the selection of sensing vector for best signal quality. In this example, a primary sensing vector has previously chosen, and the sensed cardiac signal is shown at 150, with detection markers shown below the signal 150 where "T" indicates a treatable tachyarrhythmic beat, per applied discrimination criteria. After a run of "T" markings 152, a charge begin marker is shown at 154, indicating that the device has determined, based on analysis of the signal 150, that a treatable arrhythmia is occurring. However, to the skilled artisan, it would be apparent that signal 150 is simply a very small signal that does not appear to actually demonstrate an arrhythmia.

In the hypothetical of FIG. 5, the cardiac signals for second and third vectors are shown at 160 and 170. It can be seen in the second vector 160 that a fairly normal non-arrhythmic signal is occurring with reasonable amplitude beats 162, at a rate shown illustratively as about 100 beats per minute. Likewise the third vector 170 is showing reasonable beats 172. In some examples, the concept is to switch default sensing vector selection to avoid using the signal at 150 when a better signal is available elsewhere, and the target is to define parameters to perform the analysis that would switch vectors. In other examples, the device is not able to review the other sense vectors and must rely on the existing programmed sense vector as by, for example, a device being "locked" onto a sense vector configuration until external intervention occurs. In yet other examples, sense signal quality of non-programmed vectors is not always evaluated in real time using instead periodic or occasional calls for an implanted device to perform analysis, or telemetering data out of the implanted device to an external (bedside monitor or patient programmer, for example) to perform the analysis. Thus, it would be worthwhile to distinguish between low signal quality and arrhythmia onset before evaluating the signal quality across sense vectors.

Figure 6:
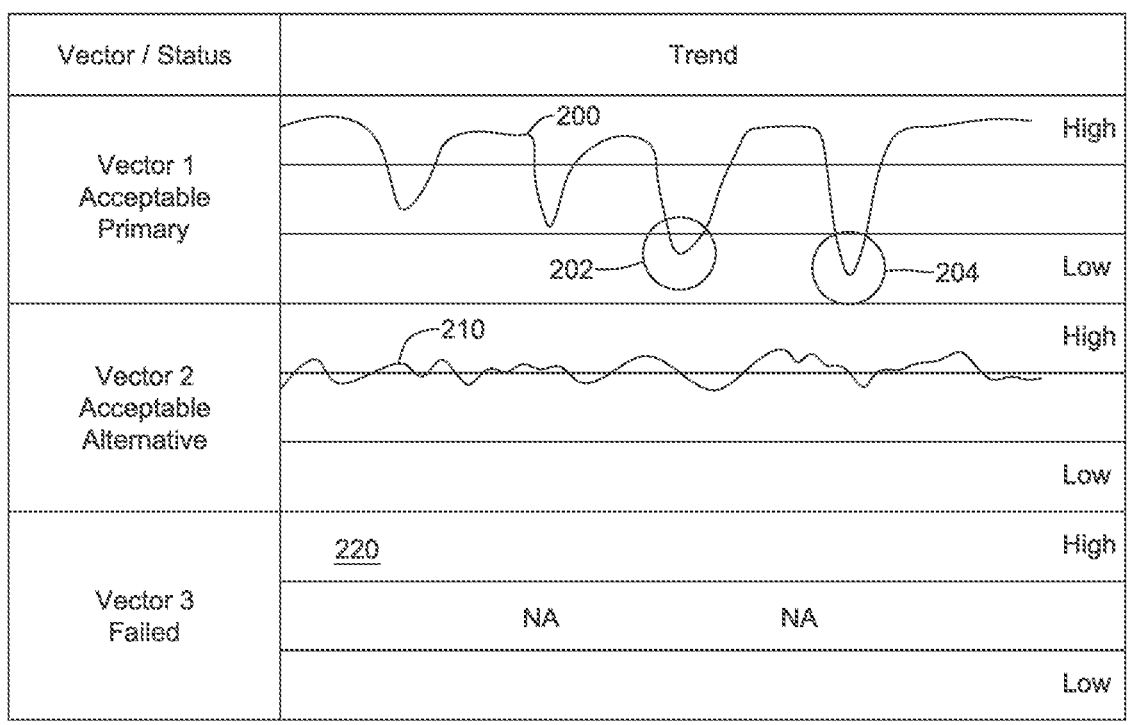
FIG. 6 illustrates graphically sensing vector signal quality metrics over time.

FIG. 6 illustrates graphically sensing vector signal quality metrics over time. The example incorporates several concepts, some of which may be used standing alone or in different combinations. A trend is shown at 200 for Vector 1, and is compared against High and Low thresholds as shown. As indicated at the left, Vector 1 in this example has been initially selected as a primary sensing vector or default sensing vector. A trend 210 is shown for another vector, Vector 2, which as indicated at the left is also considered an acceptable vector but which, at least initially, is identified as an alternative to Vector 1 in the event that Vector 1 deteriorates. As noted below, in some examples only the trend for Vector 1 may be actively tracked until a low signal quality event takes place.

Following the trend over time, Vector 2 remains at around the high quality threshold, but does not often exceed the High threshold. Vector 1, on the other hand, is well above the High threshold as shown at 200, but begins to show dips in quality over time, including dips into an "OK" region between the High and Low Thresholds. At 202, the quality dips below the Low threshold. A short time later, as shown at 204, Vector 1 again drops below the Low threshold. The repeated crossing of the Low threshold may serve as a separate trigger for reassessment of the Primary and Alternative vector designations.

The dips into the "OK" zone or the Low zone may serve as triggering events for reassessing the Primary and Alternative sense vector designations. For examples where signal quality trending is performed on multiple vectors, any time that the quality of the Alternative vector is greater than the quality of the Primary vector may also serve as a triggering event for reassessing the Primary and Alternative vector designations.

Vector 3 is shown as well, but no data is provided as indicated at 220. This may indicate that during a prior analysis Vector 3 was deemed unusable. U.S. patent application Ser. No. 15/297,568, titled SIGNAL QUALITY MONITORING FOR MULTIPLE SENSE VECTORS IN CARDIAC DEVICES, provides additional discussion of the use of trending data over time.

As highlighted with the analysis of FIGS. 8-9, one issue that can arise is that the drop in signal quality indicated at 202 and 204 for Vector 1 may result from an arrhythmia onset. In such an occasion, reassessment of sensing vectors may be futile, as all the sensing vectors are likely to demonstrate poor quality sensing and, moreover, switching sense vectors during an arrhythmia may impede accurate detection and declaration of the arrhythmia, ultimately delaying therapy. Therefore, in several examples shown below, additional analysis is performed before engaging the sense vector reconfiguration to ensure that an arrhythmia is not the source of identified sensing quality changes.

Figure 7:
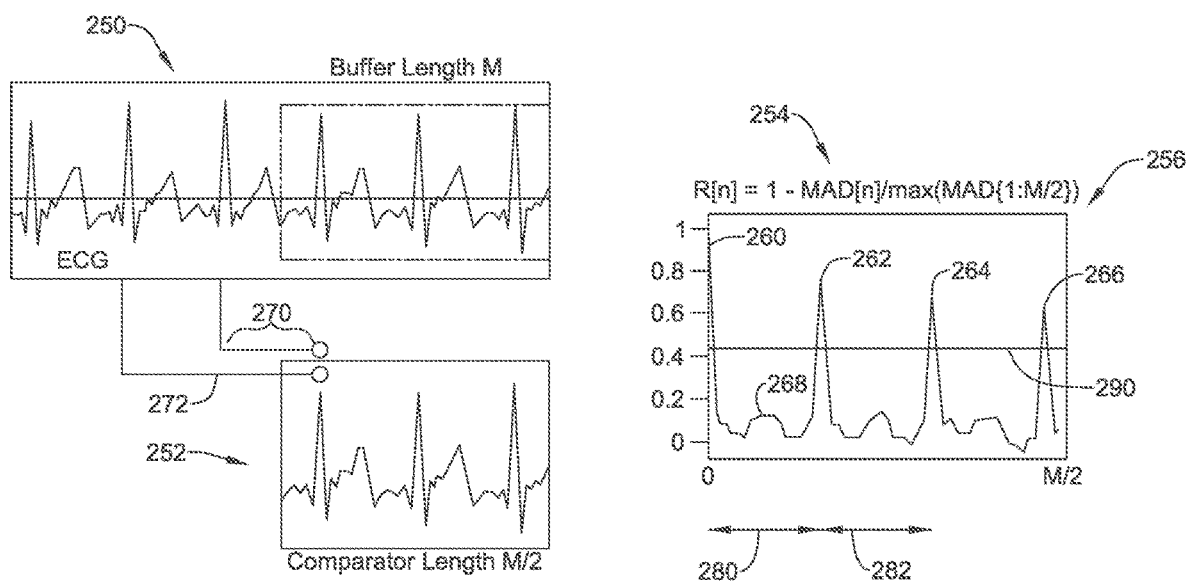
FIG. 7 demonstrates a method of cardiac rate analysis which does not rely on cardiac cycle detection.

In some examples, prior to engaging a sensing reconfiguration process, a system or device may seek to perform a second rate analysis. The second rate analysis may be performed without the use of cardiac cycle detection in several examples. FIG. 7 shows one example.

FIG. 7 demonstrates a method of cardiac rate analysis which does not rely on cardiac cycle detection. The method uses blocks of data, rather than cardiac cycle detection. The drawing and following discussion provides a high level overview of several methods that may be used for generating a second cardiac rate estimate; additional details may be found in U.S. Pat. No. 9,451,892, titled CARDIAC RATE TRACKING IN AN IMPLANTABLE MEDICAL DEVICE and U.S. Pat. No. 9,451,893, titled CALCULATION OF SELF-CORRELATION IN AN IMPLANTABLE CARDIAC DEVICE, and U.S. PG Pub. No. 2016-0045132, titled PEAK SELECTION FOR SELF CORRELATION ANALYSIS OF CARDIAC RATE IN AN IMPLANTABLE MEDICAL DEVICE, the disclosures of which are incorporated herein by reference.

The example shows a cardiac electrical signal at 250, stored in a buffer of length M. The buffer length may be, for example, from about one to about ten seconds, with four seconds serving in several illustrative embodiments. About one half of the buffer has been extracted as a "comparator", shown at 252. The comparator 252 may be shorter than one-half the buffer length in other examples. For example, the comparator 252 may have a length of about 500 milliseconds to about 2000 milliseconds, or greater or shorter, with the buffer being at least half again as long and as much as three times as long, or more, if desired.

The comparator 252 is repeatedly compared using, for example, correlation waveform analysis or difference of area subtraction, for example (or other comparative technique) to a segment of equal length from the buffer 250. Each comparison occurs at a lag depth that begins at zero, and increases until the comparator 252 has been drawn across the buffer 250 to a desired extent. For example, supposing the buffer 250 contained 512 samples of data (four seconds at 128 Hz), and the comparator contained 256 samples of data (two seconds at 128 Hz), then the comparator could be subtracted at lag depths from 0 to 256, to yield 256 data points as shown at 256, where each data point is calculated according to the formula shown at 254. The set of data points is referred to as R[n], with n indicating the lag depth. As seen at 456, a first peak appears at the lag depth of 0—at this point, the comparator 252 is actually compared to itself, yielding a perfect match valued at 1.0 in the chart 256.

As the lag depth increases, the match decreases quickly from the initial perfect match. As the lag depth continues to increase, a peak appears at 262. This peak corresponds to a lag depth illustrated at 270, in which the R-wave peaks in the comparator 252 each line up to R-wave peaks in the buffer 250. As the calculation occurs to the larger lag depths, a set of peaks emerges as shown at 262, 264, 266, with each peak appearing at a lag depth where the ECG signal peaks 250 line up with respective peaks in the comparator 252.

The next step is to determine which of the peaks in the graph 256 provides a best estimate of cardiac rate. An illustrative rule set would first throw out the peak at 260, as it is an artifact of the comparison at n=0. Next, peak 268 may be ruled out as being too short, using as an example a requirement that R[n] (formula 104) exceed a threshold 290 that can be set in the range of about 0.3 to about 0.5 (or greater or lesser if desired) for peaks to be considered. Peak 262 may be selected at the peak with the shortest lag time that exceeds the height threshold. Peak 262 may be confirmed as a high confidence estimate by determining whether one or more of peak 264 and 266 are an integer multiples of the lag depth 280 of peak 262. These integer multiple peaks 264 and 266 are referred to as "Pickets" in the noted U.S. Pat. Nos. 9,451,892 and 9,451,893, and U.S. PG Pub. No. 20160045132, which provide numerous additional examples and detailed discussions.

The lag depth 280 can be converted to a cardiac rate if the sampling rate is known. For example, a lag depth of 64 samples, at 128 hertz, gives a period of 500 milliseconds and converts to 120 BPM. In the example shown, if the data is obtained at 128 Hz, and peak 262 is at a lag depth of about n=85, the corresponding period would be 664 milliseconds (85 times 7.8 milliseconds), converting to a rate of 90 BPM. It may be noted, for confirmation of this summary explanation, that the four second buffer 250 has six sharp R-wave peaks in it, corresponding to 90 BPM.

In some examples, a specific 50 Hz or 60 Hz filter may be added to the analysis using lag depth. For example, peaks in a very high cardiac rate range of for example 300 BPM and which correlate to a multiple of the period of a 50 or 60 Hz signal may be excluded as likely corresponding to 50 or 60 Hz line noise.

At least two features should be noted with respect to FIG. 7. First, rather than finding individual cardiac cycles, the method identifies lag depths of greatest similarity of the comparator 252 to the ECG 250. Therefore the outcomes are likely to be independent of an analysis that uses individual cycle detection. Second, there are measures of confidence that can be gleaned from the graph at 256—one measure is a very high peak (R[n] of 0.5 or above, for example) which will suggest a very high match between comparator 252 and buffer 250, and therefore a likely accurate lag depth from which rate may be calculated. Another confidence measure is the presence of pickets at integer multiples of the selected peak—here, peak 262 would be at a lag depth of about n=85, and peaks 264 and 266 would be at lag depths of about n=170 and n=255, respectively. Thus the lag depth 280 is about the same as lag depth 282 between peaks 262 and 264.

In a further example, the method of FIG. 7 may be called repeatedly, such as at intervals, to provide an estimated cardiac cycle rate. The outcomes of iterations of the method may be tracked over time as described in particular in the U.S. Pat. No. 9,451,892, to establish a rate "track", where even if relatively lower confidence is obtained by a single iteration of the method, repeated, similar results may be deemed to establish a higher confidence, tracked cardiac rate.

The method of FIG. 7, above, will generally provide a higher confidence result except in the event that the intervals between cardiac cycles are inconsistent or rapidly changing. For example, even ventricular fibrillation will typically provide output peaks and event pickets associated with such peaks using the method of FIG. 7, providing a relatively high confidence rate estimate. However, atrial fibrillation, which is often associated with highly variable intervals between ventricular events, is an exception. Generally speaking, the method of FIG. 7 will not provide a high confidence output rate if ventricular cycles of inconsistent length/interval occur as a result of atrial fibrillation.

As illustrated in FIG. 7, and discussed throughout the present disclosure, the analysis performed provides both a rate and a rhythm analysis. The "rate" is determined using the lag depth that has the highest peak (particularly if the peak is above a threshold) and/or a peak that generates one or more pickets. The "rhythm" can be categorized as cyclic or non-cyclic, and is determined by the degree of confidence in the rate output. The method of FIG. 7 will generally provide high confidence for highly cyclic rhythm, and low confidence for those lacking in cyclic character. An atrial fibrillation may not be cyclic insofar as it may provide a widely varying QRS interval. Noise may be cyclic, but may provide a rate which is non-physiological—that is, too high. Ventricular fibrillation, sinus rhythm, and/or a ventricular arrhythmia may be both cyclic and in a physiologic rate range.

These rhythm-based characteristics of the non-cycle-detection method shown in FIG. 7 may be used to address signal quality changes and differentiate certain arrhythmia-related causes for apparent low signal quality from actual changes in signal quality in examples below.

Figure 10:
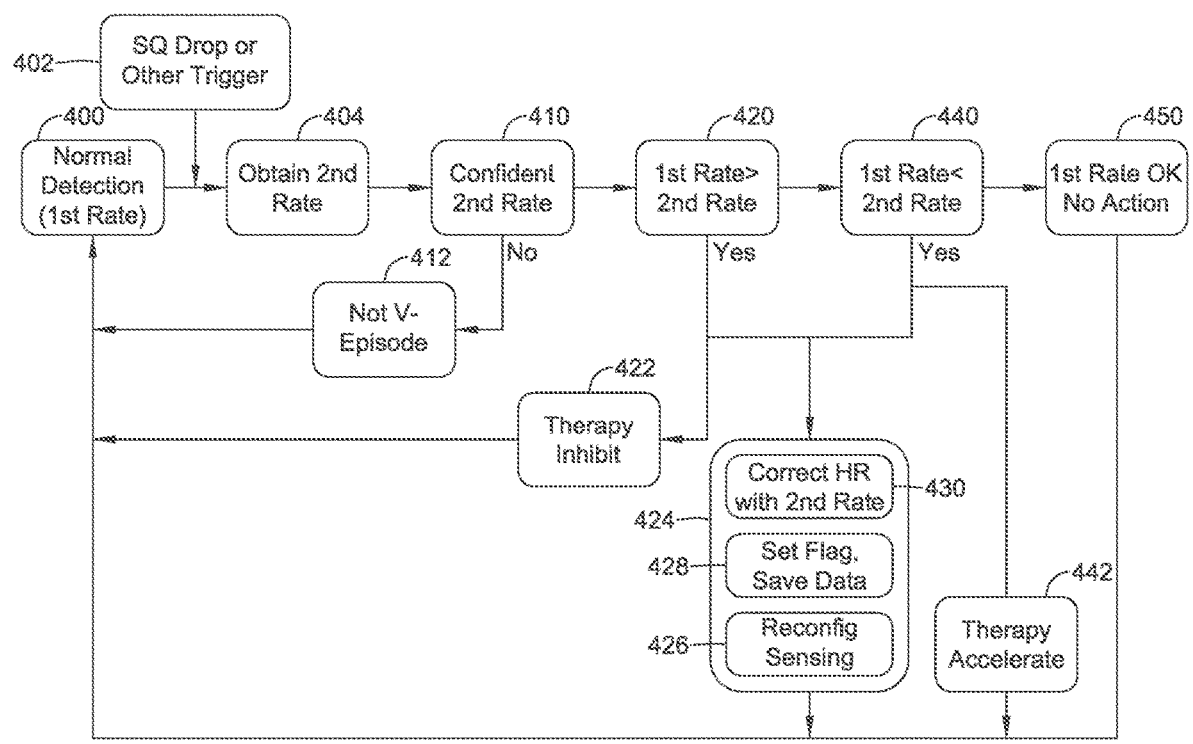
FIGS. 10, 11A-11B, and 12-14 show illustrative methods of cardiac signal analysis for use in implantable medical device systems.

FIGS. 10, 11A-11B, and 12-14 show illustrative methods of cardiac signal analysis for use in implantable medical device systems. Referring now to FIG. 10, in this illustrative example a normal or default detection mode is used at block 400 to track the cardiac rate and perform further functions for cardiac signal analysis.

A triggering condition is identified at block 402. In some examples, the triggering condition may be a reduction in the sensed signal quality. Some examples comprise, for example:

A reduction in the average R-wave amplitude over time;
Variability in R-wave amplitude;
A long pause between detected R-waves;
Detected event amplitudes near the upper or lower boundaries of the sensing range;
Repeated overdetection or repeated detection of noise;
Consistent failure to match one or plural stored templates for the sensing configuration in use;
Failure of detected QRS complexes to demonstrate consistent morphology, width, amplitude, or other shape characteristics;
Changes in spectral content of the signal sensed with a given sensing configuration;
Illustrative signal quality factors, and manners of tracking such, are also discussed in U.S. patent application Ser. No. 15/297,568, titled SIGNAL QUALITY MONITORING FOR MULTIPLE SENSE VECTORS IN CARDIAC DEVICES, the disclosure of which is incorporated herein by reference. In some examples, the triggering condition at 402 may include factors that could be caused by either a drop in signal quality or a change in the patient's cardiac condition. Some examples include detection of a significant increase or drop in the cardiac cycle rate, either in terms of a dramatic change in rate (increase or drop of more than a threshold, such as 50 BPM, over the course of a small number of cycles, such as 2-6 cycles, for example) or rate increasing over a threshold such as a tachycardia threshold in the range of 100-200 BPM, for example, 150 or 180 BPM (such a threshold may be a default setting or may be user adjustable). A trigger may also take the form of a simple timer, calling for the use of the second rate analysis at some desired interval.

Once a triggering condition is identified at 402, the method next obtains a second cardiac rate at 404. For example, the second rate may be determined using a method as illustrated above in FIG. 7. The result of the second rate analysis is then analyzed in reference to the confidence of the result, as indicated at 410. For example, using the method shown above in FIG. 7, the absence of a large peak, combined with failure to identify "pickets" as described above, will yield a low confidence result for the second rate.

In the example shown, a low confidence result as assessed at 410 leads to a conclusion that the underlying cardiac rhythm is not a ventricular arrhythmia, as indicated at 412. For example, a rhythm may be found to result from an underlying signal quality issue such as baseline wander or noise, causing cyclic similarity at non-physiologic rates. On the other hand, some cardiac conditions may interrupt cyclic similarity of the sensed signals. For example, noise may be identified by looking for a stable rate pattern that is above a defined threshold such as 280 BPM, suggesting noise from an external electrical source or even lead fracture. Atrial fibrillation may generate instability in a cyclic analysis and may be further confirmed using secondary measures such as witnessing absence of a P-wave or as described in U.S. Pat. Nos. 9,307,920 and/or 8,827,895. If an atrial arrhythmia is identified, an episode of such may be recorded and/or a flag may be set to indicate atrial arrhythmia burden, if desired. Noise conditions may likewise trigger a flag or recording of data.

As noted above, relative to FIG. 7, if the ventricular cycles are caused by atrial fibrillation, the resulting R-R intervals may be quite variable, preventing the comparator (252 in FIG. 7) from yielding a strong match to the buffer (250 in FIG. 7) at any lag depth. A low confidence result 412 will then revert the method to the normal detection state 400. The overall process may be iterative such that even if a low confidence result 412 occurs one or more times, if tracking is enabled for the second cardiac rate and shows that, over time, the same result, even if low confidence individually, is occurring repeatedly, this may be treated as high confidence, passing the method to block 420 rather than block 412.

In some examples, each of pickets and tracking may be used for determining confidence in block 410. For example, if analysis as in FIG. 7 is performed, and the result is a peak that lacks corresponding pickets, this may be deemed low confidence unless the result is repeated in a next iteration of the same method occurring at a later time (such as one to five seconds later). If neither pickets nor a track appear, this may be one example of a low confidence result. Other examples may rely only on the existence of tracking over multiple iterations, or may rely only on the existence of pickets.

At block 420, it is determined whether the first calculated rate exceeds the second calculated rate, as shown. If so, this may indicate that the normal detection is generating overdetections. A first response may be to inhibit therapy as indicated at 422. Therapy inhibition may include, for example, setting a timer that bars therapy preparation or delivery until expiration thereof, by adjusting a counter such as an X/Y counter, persistence counter, or confirmation counter, to require additional incoming data before therapy can be delivered or preparations for therapy can begin.

If block 420 yields a "Yes", additional corrective actions may also or instead take place, as indicated at 424. For example, the sensing setup may be reconfigured, as indicated at 426, by re-selecting a sensing vector or combination of vectors, or adjusting filtering or other settings. A static template used to analyze cardiac signals may be re-selected, if desired. At 428, a flag may be set and data saved for later retrieval and use by a physician or other authorized person to determine what occurred and why, and to make any suitable setting changes as needed. In some examples, prior data relying on the normal detection activity in block 400 may be corrected using the second cardiac cycle rate, as indicated at 430. Again the method can then return to block 400, with any relevant adjustments having been made.

Going back to block 420, if the first rate is not higher than the second rate, the method next checks whether the first rate is lower than the second rate, which may suggested undersensing. If so, the method may take steps to accelerate therapy delivery, as indicated at 442. Block 442 may represent a direct call to begin therapy preparations or deliver a therapy that is already prepared. In other examples, block 442 may comprise modifying one or more variables used in the overall method of cardiac arrhythmia detection by, for example, increasing the value of X in an X-out-of-Y filter, removing or reducing a persistence requirement, or reducing an evidence requirement for charge confirmation or shock confirmation.

In some examples, a system using the method of FIG. 10 may call for delivering ATP prior to delivering a defibrillation shock; block 442 may bypass the ATP step if desired. Further changes may also be called for if the first rate is less than the second rate at block 440, again using the adjustments within block 424 to reconfigure sensing 426, set a flag and save data 428, and/or make adjustments to stored cardiac cycle rate data 430.

Finally, failing both of 420 and 440, the system may determine at block 450 that the first rate and second rate are equal or at least similar within predetermined bounds. For example, the method may be performed using some set of parameters to allow a band of "equal" rates, such as +/−10%, or +/−20 BPM, or other bands, to be deemed neither greater than nor less than for purposes of comparisons 420 and 440. In essence the first rate is found to be accurate, and the method returns to block 400. As an alternative, given that the triggering condition took place 402, and if the trigger was something indicating a reduction in signal quality, the system may perform a reconfiguration of sensing to adjust vector selection and/or filtering, or template storage, or other setting, variable or data. In one example, a system may be configured to sense/analyze using a single sense vector, or a selected subset of available sense vectors during normal operation, and a triggering condition at block 402 may open up analysis to look at all available sense vectors.

In several examples, the rate 404 is a second rate not reliant on cardiac cycle detection that can be performed within the same device that performs the first rate analysis using the cardiac electrical signal. In some alternatives, the second rate may be obtained by requesting a rate measurement from a second device. For example, an implantable system having a canister and a lead as shown in FIG. 1 may communicate with a second device such as a leadless cardiac pacemaker, and may obtain a rate therefrom. Such communication may be of particular use if a noise or other condition is affecting one device more than the other, for example. A noise alert and any suitable mitigation may be performed as well, if desired.

In another example, a non-cardiac electrical signal may be used by obtaining an output from a heart sound sensor, a pressure monitor in or coupled to a blood vessel, a cardiac motion detector, an oximetry device, or other sensor. Such non-cardiac electrical signals may be captured by the device/system itself, or may be captured by a separate device in communicative contact (such as via Bluetooth, inductive telemetry, RF communication, or conducted communication, for example) with the device/system. For such other methods of obtaining a second rate, confidence measures may be used again, such as by allowing the second rate to be calculated while tracking the underlying signal (sound, motion, optical or others) against amplitude, intensity, noise, variability or other thresholds.

In some examples, a triggering condition may be set in a manner that calls for assessment using a second rate calculation before the device begins tracking an arrhythmia. For example, a reduction in signal quality may be identified using factors such as a drop in amplitude, variability in amplitude, repeated overdetection or noise detection, etc. before an increase in the calculated rate takes place. Waiting for the cardiac rate to increase may make the patient more susceptible to inappropriate shock due to poor sensing. Thus an early check of the signal quality can be performed using amplitude, rather than rate, where amplitude drop may be identified within one or two cardiac cycles, while rate may be calculated using for example four cardiac cycles (the "4RR average" for example). A rhythm analysis may use even more detected events such as a device having a VF NID of 8, where eight detections at very high rate (in a VF zone) would be needed, or a device using an X-out-of-Y filter set to 18 out of 24. By using possible sensing quality changes as a trigger for additional analysis, an underlying sensing issue can be identified sooner than other rate based or rhythm based triggers may allow, though as noted, the assessment of sensing quality using a second cardiac rate calculation may be performed repeatedly.

In some examples, recheck of the second cardiac rate at 404 may be performed repeatedly as different trigger points are met. For example, if the signal drops in amplitude, a second rate may be calculated a first time. If an arrhythmia is found and persists, once the calculated average rate exceeds a threshold, a second recheck can be performed. If the arrhythmia still persists, another recheck may be performed prior to calling for charging for high energy therapy. The recheck may again be called prior to shock delivery. Referring back to FIG. 4, for example, a recheck may be performed in block 102, again prior to passing from block 100 to block 120, again before passing from block 120 to block 130, and still one more time at block 134, for example.

If a ventricular arrhythmia is not found—that is, the signal is not found to be cyclic in nature, suggesting a supraventricular arrhythmia—then the system may set a flag or alert that there is the potential for inappropriate shock to occur, facilitating additional data capture if needed or otherwise issuing a notification.

Figure 11A:
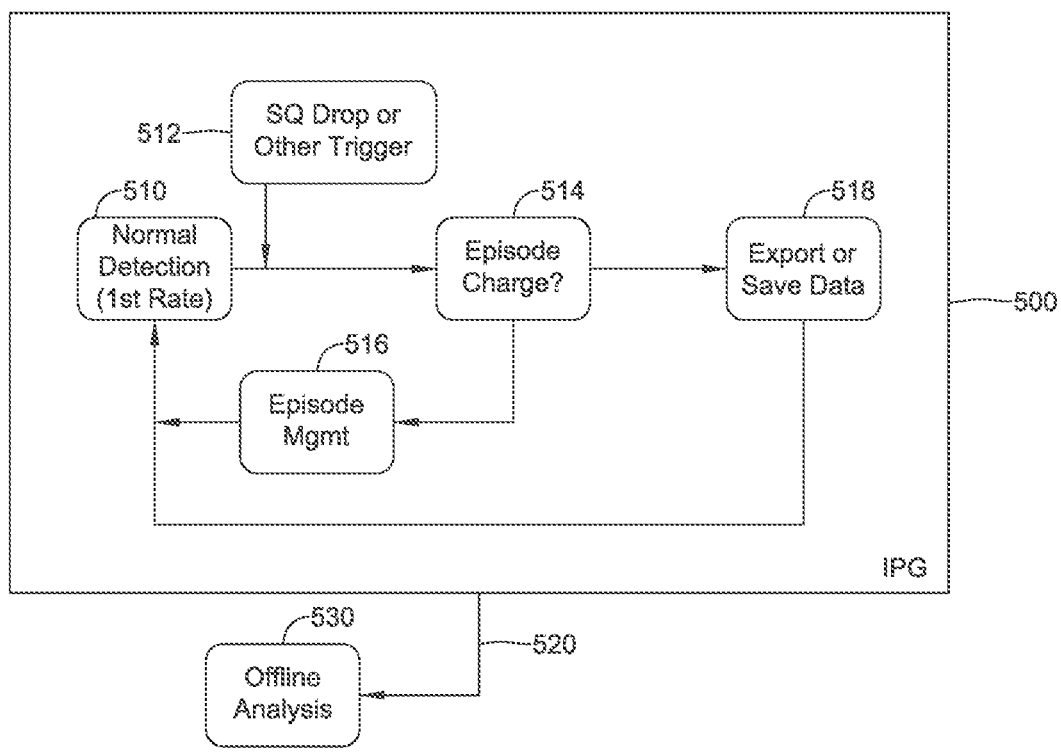
Figure 11B:
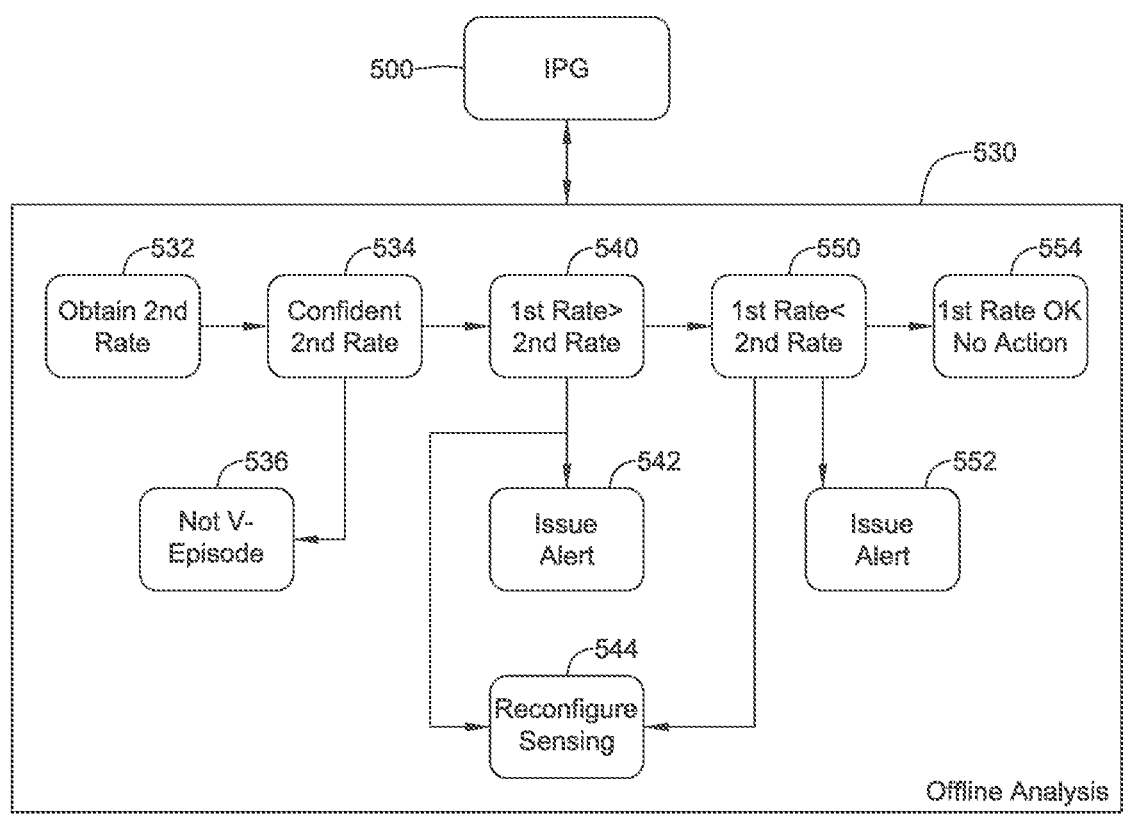

FIG. 10 is generally directed at an illustrative example in which a device or implanted system autonomously determines next steps in response to the identification of a triggering condition. FIGS. 11A-11B show an alternative in which an implantable device operates in conjunction with one or more external devices that support offline analysis.

Referring to FIG. 11A, an implantable pulse generator performs several parts of an illustrative method. Again there is a normal or default operation to generate a first cardiac rate, as indicated at 510. In response to a triggering condition 512 (which may be similar to triggering conditions noted relative to block 402 in FIG. 10), the device determines whether an episode of arrhythmia, or capacitor charging for high energy therapy delivery, has occurred or been initiated at 514. If so, then episode management tools 516 are used to handle any next steps including, for example, therapy delivery (see FIG. 4, above, for example). If no episode or charging initiation occurs, the device exports and/or saves data related to the underlying conditions that caused the trigger 512. Such data is then communicated 520 for offline analysis using an external device 530. For example, communication 520 may be to a bedside monitor for the IPG 500 or to a patient's mobile device such as a cellphone having Bluetooth capability.

FIG. 11B illustrates the offline analysis. Such analysis may be performed by the device communicating with the IPG as by, for example, having a patient's cellphone or a bedside monitor run programming code and instructions to perform detailed analysis as indicated. In other examples, the offline analysis may be performed at a central server which may be administered by a clinic or hospital or by a medical device manufacturer.

The offline analysis begins with obtaining a second cardiac rate using a more sophisticated or computationally intensive approach than that which the IPG 500 is capable of, as indicated at 532. For example, a method as in FIG. 7 may be performed offline to avoid the increased computational burden and power consumption that would be needed in an IPG 500 (as noted, FIG. 10 above, and various examples herein, do call for the IPG to perform this type of analysis, such that this particular method of FIGS. 11A-11B should not be deemed limiting or restrictive of these other alternatives).

Next, if there is no confidence in the second rate 534, the method can determine that the underling rhythm was not a ventricular episode, as indicated at 536. If desired, further analysis may be performed to further confirm whether an atrial arrhythmia such as atrial fibrillation has been taking place. For example, beat to beat morphology with atrial fibrillation is typically fairly high, though intervals between such beats may vary; a secondary analysis of correlation from one beat to the next may be performed to confirm atrial fibrillation if desired.

A flag may be set to indicate atrial arrhythmia burden, if desired, and the physician or patient may be notified. If the patient is notified of atrial arrhythmia, such a notification may be accompanied by queries to aid in determining whether the patient is showing any symptoms of the atrial arrhythmia, or with a reminder to ensure the patient is taking any appropriate medication.

If the second rate is returned with high confidence (using for example, one or more of pickets, peak height, or tracking, as explained above), the offline analysis determines whether the first rate exceeds the second rate, as indicated at 540. If so, an alert may be issued to the patient or physician, as indicated at 542, indicating that something is awry with the sensing of the device. In some examples, as indicated at 544, the offline analysis may conclude with a command to the IPG 500 to reconfigure its sensing. Offline analysis may be used to differentiate arrhythmia sensing causing low signal quality, such as atrial fibrillation, from noise, as described above. If noise can be found, an alert may issue to make the patient aware that noise was encountered. Such awareness may be useful if, for example, the patient was engaged in an activity without realizing the activity could affect device operation (use of an arc welder, or coming into contact with poorly insulated or improperly grounded electric lines or devices, for example).

Failing at 540, the method next checks whether the first rate is less than the second rate, indicating potential undersensing. If so, an alert may again be issued to the patient and/or physician, as indicated at 552, that undersensing appears likely and the patient may potentially need assistance. In some examples, the external device may, again, take the additional step of issuing a command to reconfigure sensing 544.

If each of 540 and 550 fail, then the first rate and second rate are similar or equal, and no action is necessary, as indicated at 554. If desired, a report may be generated and sent to the IPG 500 or to the physician or a central server, to allow logging of the underlying analysis having taking place, confirming appropriate rate detection in the IPG 500.

Figure 12:
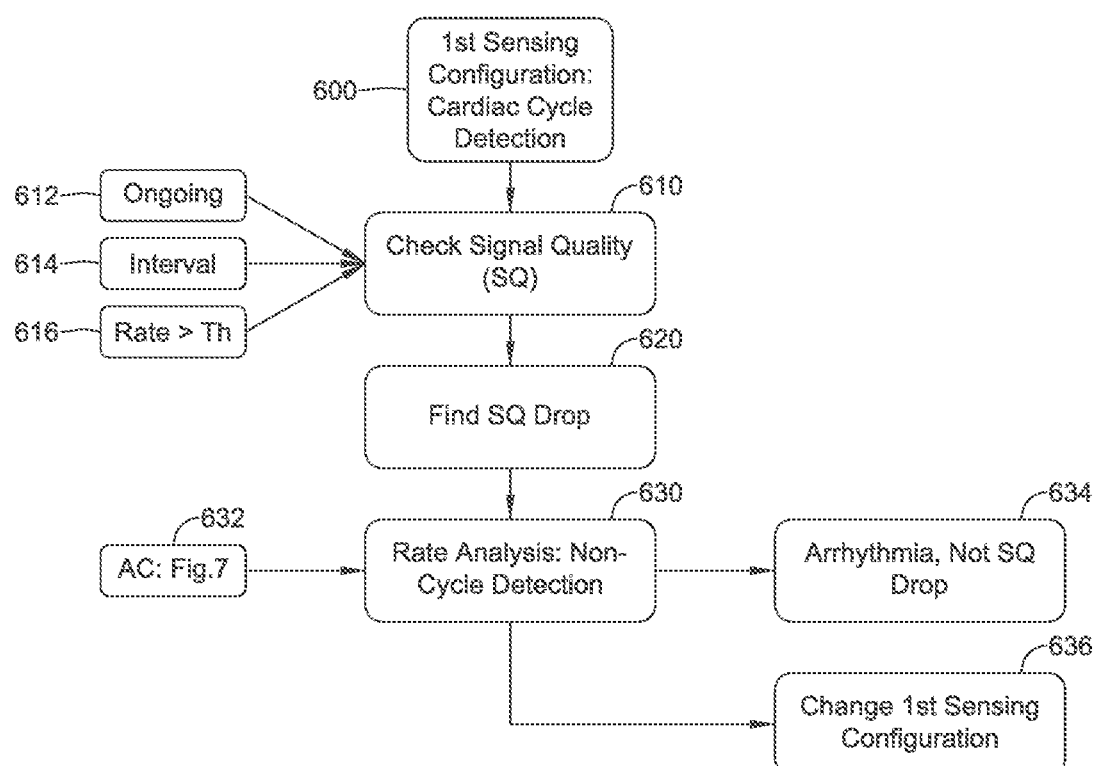

FIG. 12 shows another illustrative example. In this example, a method of cardiac signal discrimination in an implantable cardiac device is shown in block form. At block 600, the device/method monitors a first sensing configuration to determine whether an arrhythmia is occurring by the use of cardiac cycle detection to detect cardiac cycles. Using such cycles, the device can estimate cardiac rate and perform the analysis of morphology or other factors as needed using an architecture/algorithm as described above in FIG. 4. At block 610, the device/method checks a signal quality of the first sensing configuration. Such checking may be performed using the various factors above (amplitude, signal to noise ratio, noisy or overdetected events, etc.) that are described relative to a triggering condition, for example. The signal quality check 610 may be performed on an ongoing basis 612 such as at each detected cardiac cycle or each nth detected cardiac cycle, or at intervals 614 such as once every few seconds, or may be performed in response to finding that the detected cardiac cycle rate has exceeded a threshold as shown at 616.

In the illustrative method/device, a likely drop in sensing quality of the first sensing configuration is identified as indicated at 620. Such a drop may be identified by the use of a threshold. For example, if the R-wave amplitude is monitored and is above one millivolt this may not suggest a drop in quality, but if the amplitude drops below one millivolt (or other measured level, which may vary depending on sensing electrode placement and spacing), this may be drop. In another example, signal to noise ratio of greater that 2:1 may be deemed acceptable/preferable, and dropping below 2:1 (or other ratio such as 3:2, if desired) may be considered a drop in signal quality; signal to noise ratio can be measured in various ways such as by comparison of R-wave amplitude to T-wave amplitude, or R-wave amplitude to the root-mean-square amplitude across an entire cardiac cycle, or other measures. A drop in signal quality may be identified if a threshold quantity of noisy or overdetected cardiac cycles are identified in some examples such as by determining if some quantity of such determinations has occurred in a set period of time or within a select quantity of cardiac cycles, for example. Other measures may be used.

Next the illustrative method/device, in response to the likely drop in sensing quality of the first sensing configuration, performs a rate analysis of the patient's cardiac signal using a method other than cardiac cycle detection, as indicated at 630. For example, a method relying on spectral analysis, frequency analysis, or the use of blocks of data as discussed and shown above in relation to FIG. 7 (as indicated at 632) may be used. Using this second rate analysis, the method/device then determines whether the actual underlying cardiac signal reflects an arrhythmia rather than a sensing quality drop, as indicated at 634, or confirms that the signal quality has fallen and therefore determines that the first sensing configuration should be changed, as indicated at 636.

In an illustrative example, in block 630, the method/device may compare a first rate calculated at 600 to a second rate calculated at 630; if the rates match, this would lead to block 634. If the second rate is higher than the first rate, this again may suggest an arrhythmia 634 if for example the rates are elevated to an arrhythmia detection zone such as a VT or VF zone. If the second rate is less than the first rate, the result would be to change the first sensing configuration 636. In some examples, block 610 may be called in response to an elevated rate condition as indicated at 616, when this is the case, the second rate exceeding the first rate may automatically trigger block 634. In parallel, the method or system optionally may also analyze one or more additional sensing configurations, if desired, to determine if the arrhythmia can be better detected using a different configuration.

In an alternative illustrative example, particularly if block 616 is not the basis for performing the signal quality check at 610, anytime the rates mismatch at block 630, block 636 may be called to at least assess a change to the first sensing configuration. Block 634 may be called if either the rates match, or if the non-cardiac cycle detection second rate is in an arrhythmia zone with indications of high confidence in the second rate. For some embodiments, both blocks 634 and 636 may be activated.

In one example, if the second rate at 630 does not match the first rate from block 600, and the second rate at block 630 is below an arrhythmia zone, block 636 is called and block 634 is not. Further in this example, if the second rate at 630 does not match the first rate from block 600 and is in an arrhythmia zone, block 634 is called. Finally, if the first rate from block 600 matches the second rate from block 630, the system determines an arrhythmia is occurring, triggering block 634, and may also determine that sensing configuration should be reassessed, calling 636 as well.

Figure 13:
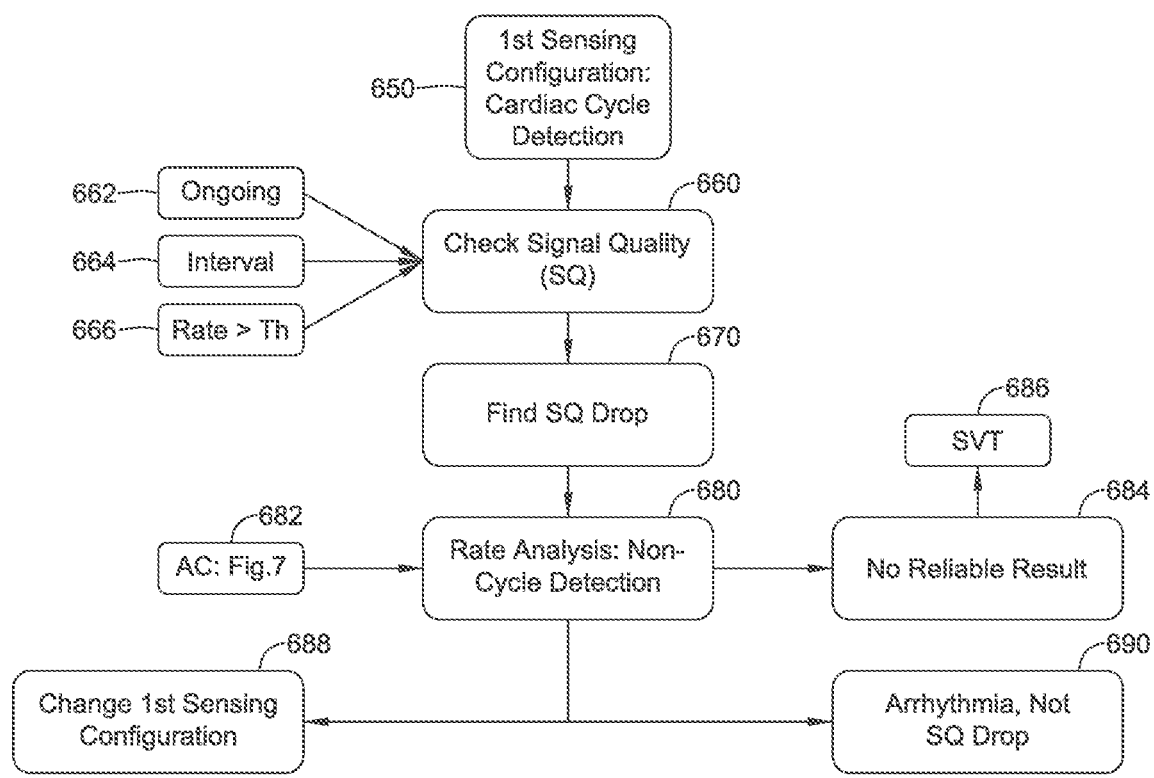

FIG. 13 shows another illustrative example. In this example, a method of cardiac signal discrimination in an implantable cardiac device is shown in block form. At block 650, the device/method monitors a first sensing configuration to determine whether an arrhythmia is occurring by the use of cardiac cycle detection to detect cardiac cycles. Using such cycles, the device can estimate cardiac rate and perform the analysis of morphology or other factors as needed using an architecture/algorithm as described above in FIG. 4. At block 660, the device/method checks a signal quality of the first sensing configuration. Such checking may be performed using the various factors above (amplitude, signal to noise ratio, noisy or overdetected events, etc.) that are described relative to a triggering condition, for example. The signal quality check 660 may be performed on an ongoing basis 662 such as at each detected cardiac cycle or each nth detected cardiac cycle, or at intervals 664 such as once every few seconds, or may be performed in response to finding that the detected first rate has exceeded a threshold as shown at 666.

In the illustrative method/device, a likely drop in sensing quality of the first sensing configuration is identified as indicated at 670. Such a drop may be identified by the use of a threshold. For example, if the R-wave amplitude is monitored and is above one millivolt this may not suggest a drop in quality, but if the amplitude drops below one millivolt (or other measured level, which may vary depending on sensing electrode placement and spacing), this may be drop. In another example, signal to noise ratio of greater that 2:1 may be deemed acceptable/preferable, and dropping below 2:1 (or other ratio such as 3:2, if desired) may be considered a drop in signal quality; signal to noise ratio can be measured in various ways such as by comparison of R-wave amplitude to T-wave amplitude, or R-wave amplitude to the root-mean-square amplitude across an entire cardiac cycle, or other measures. A drop in signal quality may be identified if a threshold quantity of noisy or overdetected cardiac cycles are identified in some examples such as by determining if some quantity of such determinations has occurred in a set period of time or within a select quantity of cardiac cycles, for example. Other measures may be used.

Next the illustrative method/device, in response to the likely drop in sensing quality of the first sensing configuration, performs a rate analysis of the patient's cardiac signal using a method other than cardiac cycle detection, as indicated at 680. For example, a method relying on spectral analysis, frequency analysis, or the use of blocks of data as discussed and shown above in relation to FIG. 7 (as indicated at 682) may be used.

As discussed above, there may be input data for a method as in FIG. 7 that fails to provide a reliable result. One example is if an atrial arrhythmia, such as atrial fibrillation, causes variable R-R intervals. Other examples may include exogenous electrical signals causing noise. If no reliable result can be had, as indicated at 684, the example shown concludes that an SVT is likely, as indicated at 686. The SVT may be atrial fibrillation, for example. If block 686 is reached, the system may record data for an episode of atrial arrhythmia. Further analysis may be called to confirm variable R-R intervals, if desired before making a conclusive assessment. In some examples, a device may issue an alert to a remote device in order to let a physician or caregiver know of the condition. The patient may be alerted and, if desired a system may issue one or more patient queries to determine whether the patient is suffering any symptoms of the atrial arrhythmia.

If the second rate analysis 680 does give a reliable or high confidence result, the method/device then determines whether the actual underlying cardiac signal reflects an arrhythmia rather than a sensing quality drop, suggesting in turn a need to reconfigure sensing, as indicated at 688, or confirms that the signal quality has fallen and therefore determines that the first sensing configuration should be changed, as indicated at 690.

In an illustrative example, in block 680, the method/device may compare a first rate calculated at 650 to a second rate calculated at 680; if the rates match, this would lead to block 690. If the second rate is higher than the first rate, this again may suggest an arrhythmia 690 if for example the rates are elevated to an arrhythmia detection zone such as a VT or VF zone. If the second rate is less than the first rate, the result would be to change the first sensing configuration 688. In some examples, block 660 may be called in response to an elevated rate condition as indicated at 666, when this is the case, the second rate exceeding the first rate may automatically trigger block 690. In parallel, the method or system optionally may also analyze one or more additional sensing configurations, if desired, to determine if the arrhythmia can be better detected using a different configuration.

In an alternative illustrative example, particularly if block 666 is not the basis for performing the signal quality check at 660, anytime the rates mismatch at block 680, block 688 may be called to at least assess a change to the first sensing configuration. Block 690 may be called if either the rates match, or if the non-cardiac cycle detection second rate is in an arrhythmia zone with indications of high confidence in the second rate. For some embodiments, both blocks 688 and 690 may be activated.

In one example, if the second rate at 680 does not match the first rate from block 650, and the second rate at block 680 is below an arrhythmia zone, block 688 is called and block 690 is not. Further in this example, if the second rate at 680 does not match the first rate from block 650 and is in an arrhythmia zone, block 690 is called. Finally, if the first rate from block 650 matches the second rate from block 680, the system determines an arrhythmia is occurring 690, and may also determine that sensing configuration should be reassessed, calling 688 as well.

Figure 14:
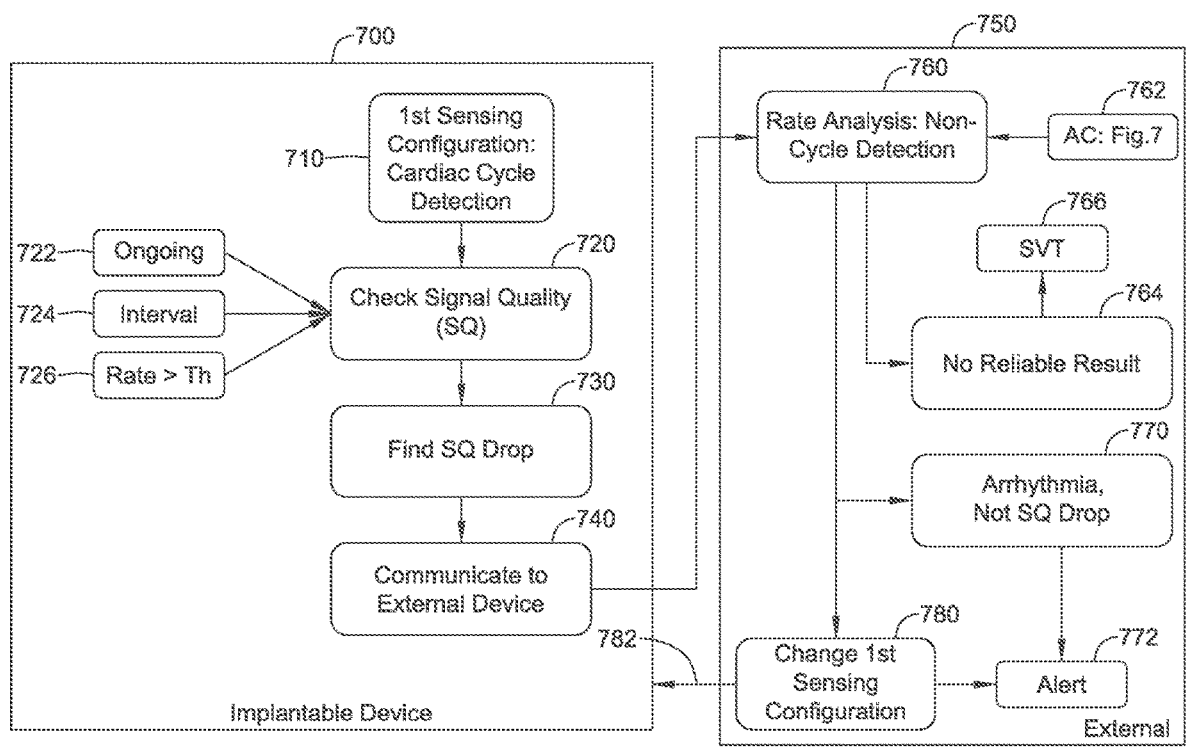

FIG. 14 shows another illustrative example. In this example, a method of cardiac signal discrimination in an implantable cardiac device is shown in block form, with elements of the system being both in an implantable device such as an implantable pulse generator 700, as well as in an external device 750 which may be a patient's mobile device, a patient controller device, a bedside monitor, or a physician programmer. At block 710, the implantable device 700 monitors a first sensing configuration to determine whether an arrhythmia is occurring by the use of cardiac cycle detection to detect cardiac cycles. Using such cycles, the implantable device 700 can estimate cardiac rate and perform the analysis of morphology or other factors as needed using an architecture/algorithm as described above in FIG. 4. At block 720, the implantable device checks a signal quality of the first sensing configuration. Such checking may be performed using the various factors above (amplitude, signal to noise ratio, noisy or overdetected events, etc.) that are described relative to a triggering condition, for example. The signal quality check 720 may be performed on an ongoing basis 722 such as at each detected cardiac cycle or each nth detected cardiac cycle, or at intervals 724 such as once every few seconds, or may be performed in response to finding that the detected first rate has exceeded a threshold as shown at 726, for example.

In the illustrative implantable device 700, a likely drop in sensing quality of the first sensing configuration is identified as indicated at 730. Such a drop may be identified by the use of a threshold. For example, if the R-wave amplitude is monitored and is above one millivolt this may not suggest a drop in quality, but if the amplitude drops below one millivolt (or other measured level, which may vary depending on sensing electrode placement and spacing), this may be drop. In another example, signal to noise ratio of greater that 2:1 may be deemed acceptable/preferable, and dropping below 2:1 (or other ratio such as 3:2, if desired) may be considered a drop in signal quality; signal to noise ratio can be measured in various ways such as by comparison of R-wave amplitude to T-wave amplitude, or R-wave amplitude to the root-mean-square amplitude across an entire cardiac cycle, or other measures. A drop in signal quality may be identified if a threshold quantity of noisy or overdetected cardiac cycles is identified in some examples such as by determining if some quantity of such determinations has occurred in a set period of time or within a select quantity of cardiac cycles, for example. Other measures may be used.

Next the illustrative implantable device, in response to the likely drop in sensing quality of the first sensing configuration, communicates data to the external device 750, as indicated at 740.

The external device 750 receives the communicated data and performs a rate analysis of the patient's cardiac signal using a method other than cardiac cycle detection, as indicated at 760. For example, a method relying on spectral analysis, frequency analysis, or the use of blocks of data as discussed and shown above in relation to FIG. 7 (as indicated at 762) may be used.

As discussed above, there may be input data for a method as in FIG. 7 that fails to provide a reliable result. One example is if an atrial arrhythmia, such as atrial fibrillation, causes variable R-R intervals. If no reliable result can be had, as indicated at 764, the example shown concludes that an SVT is likely, as indicated at 766. The SVT may be atrial fibrillation, for example. If block 766 is reached, the system may record data for an episode of atrial arrhythmia. Further analysis may be called to confirm variable R-R intervals, if desired before making a conclusive assessment. In some examples, the external device 750 or the implantable device 700 may alert the patient. The external device 750 may issue an alert to a remote device in order to let a physician or caregiver know of the condition. If desired, the external device 750 may issue one or more patient queries to determine whether the patient is suffering any symptoms of the atrial arrhythmia.

If the second rate analysis 760 does give a reliable or high confidence result, the external device 750 then determines whether the actual underlying cardiac signal reflects an arrhythmia rather than a sensing quality drop, suggesting in turn a need to reconfigure sensing, as indicated at 770, or confirms that the signal quality has fallen and therefore determines that the first sensing configuration should be changed, as indicated at 780. Again, either of these outcomes 770, 780 may result in issuing an alert to the patient or a physician, as indicated at 772. If reconfiguration is needed, as indicated at 782, the external device 750 may issue a request, command, or simply a notification, to the implantable device 700 requesting, commanding, or indicating, a change to the sensing configuration or reassessment thereof.

In an illustrative example, in block 760, the external device may compare a first rate calculated at 710 to a second rate calculated at 760; if the rates match, this would lead to block 770. If the second rate is higher than the first rate, this again may suggest an arrhythmia 770 if for example the rates are elevated to an arrhythmia detection zone such as a VT or VF zone. If the second rate is less than the first rate, the result would be to change the first sensing configuration 780. In some examples, block 720 and hence block 760 may be called in response to an elevated rate condition as indicated at 726, when this is the case, the second rate exceeding the first rate may automatically trigger block 770. In parallel, the implantable device 700, with or without the aid of the external device 750, optionally may also analyze one or more additional sensing configurations, if desired, to determine if the arrhythmia can be better detected using a different configuration.

In an alternative illustrative example, particularly if block 726 is not the basis for performing the signal quality check at 720, anytime the rates mismatch at block 760, block 780 may be called to at least assess a change to the first sensing configuration. Block 770 may be called if either the rates match, or if the non-cardiac cycle detection second rate is in an arrhythmia zone with indications of high confidence in the second rate. For some embodiments, both blocks 770 and 780 may be activated.

In one example, if the second rate at 760 does not match the first rate from block 710, and the second rate at block 760 is below an arrhythmia zone, block 780 is called and block 770 is not. Further in this example, if the second rate at 760 does not match the first rate from block 710 and is in an arrhythmia zone, block 690 is called. Finally, if the first rate from block 650 matches the rate from block 680, the system determines an arrhythmia is occurring 690, and may also determine that sensing configuration should be reassessed, calling 688 as well.

Some implementations include operational circuitry for receiving a signal from implantable electrodes, processing the signal and analyzing the processed signal to make decisions such as whether to store data or deliver therapy. Operational circuitry may be housed in a canister or canisters and hermetically sealed for implantation. The operational circuitry may include a controller (such as a microcontroller or microprocessor, or simply one or more application specific integrated chip (ASIC) such as an analog, mixed signal, or digital ASIC). The operational circuitry may include suitable analog and/or digital circuits needed for signal processing, memory storage and generation of high-power electrical, low-power electrical and/or non-electrical outputs. Memory circuits may take any suitable form such as Flash memory, RAM or ROM, or any suitable memory structure. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

Implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer and implantable device may communicate with one another using, for example and without limitation, inductive or RF telemetry, or any other suitable communication solution, including conducted communication in which a field generated between two electrodes on a first device, either on the skin of the patient or implanted in the patient, is detected by a second device such that the two devices use the patient tissue as a conductive medium for communication.

Two implanted devices may use conducted communication or any other suitable communication mode to exchange data or communicate commands in two-way or one-way communication. The present invention may be embodied in a system having any such characteristics.

A first non-limiting embodiment takes the form of an implantable medical device comprising a plurality of electrodes adapted for sensing cardiac signals of a patient and operational circuitry coupled to the plurality of electrodes such that a plurality of sensing configurations among the sensing electrodes and one or more input circuits of the operational circuitry are available to the operational circuitry (such a device is shown in FIG. 1 including a canister 12 housing operational circuitry described above and a lead 14 with electrodes 16, 18, 20 defining multiple sense vectors). Further in the first non-limiting embodiment, the operational circuitry comprises: detection means for using a selected sensing configuration of the sensing electrodes and one or more input circuits to detect cardiac cycles (see, for example, detection block 100 in FIG. 4 having cycle detection at block 102, as well as normal detection 400 in FIG. 10, and the use of cycle detection in 600 in FIG. 12 and block 650 of FIG. 13). Further in the first non-limiting embodiment, there may be a first rate calculation means to use the detected cardiac cycles to calculate a first cardiac rate (noted at detection block 100 in FIG. 4 at rate calculating block 106, for example). Further in the first non-limiting embodiment there may be a second rate calculation means for performing a rate analysis of the patient's cardiac signal using a method other than cardiac cycle detection to generate a second cardiac rate and a confidence (FIG. 7 shows operation of such a means, and it is included in several illustrations including FIG. 10 at 404, FIG. 12 at 630, FIG. 13 at 680). Further in the first non-limiting embodiment there may be signal quality monitoring means to monitor a signal quality of the selected sensing configuration (such means would be integrated in block 402 of FIG. 10, block 610 in FIG. 12, block 660 in FIG. 13, and may operate as shown in FIG. 6 and as explained above). Further in the first non-limiting embodiment there may be triggering means to identify a likely drop in sensing quality of the first sensing configuration and cause the operational circuitry to use the second rate calculation means to generate a second cardiac rate and a confidence (the use of this analysis for triggering is shown by block 402 of FIG. 10 which triggers block 404, and also indicated at 620 in FIG. 12 which triggers block 630, and 670 in FIG. 13 which triggers block 680). Further in the first non-limiting embodiment, there may be arrhythmia determining means configured to determine that an arrhythmia is occurring using at least the confidence of the rate analysis. Further in the first non-limiting embodiment there may be reconfiguring means adapted to cause reconfiguration of the first sensing configuration in response to a combination of two or more of the first cardiac rate, the second cardiac rate, and the confidence (such is shown at 426 in FIG. 10, 636 in FIG. 12, and 688 in FIG. 13). In the first example and the alternatives that follow, each such means may take the form of a dedicated circuitry block such as an application specific integrated circuit or a set of analog and/or digital logic and other circuitry, or may include operational instructions stored in a memory location for operation by a processor or controller and/or state machine configured to operate in accordance with the descriptions associated with the reference blocks and figures noted, as well as any equivalents thereto.

Additionally or alternatively to the first non-limiting embodiment, the arrhythmia determining means is adapted to find that a supraventricular arrhythmia is occurring in response to finding that the confidence is low (as indicated at 412 in FIG. 10 and 684, 686 in FIG. 13), and the arrhythmia determining means is further configured to prevent the reconfiguring means from causing reconfiguration of the first sensing configuration when a supraventricular arrhythmia is occurring (as illustrated by the flow structure of each of FIGS. 10 and 13).

Additionally or alternatively to the first non-limiting embodiment, the arrhythmia determining means is adapted to find that a ventricular arrhythmia is occurring in response to finding that the second cardiac rate exceeds the first cardiac rate and is in an arrhythmia zone (see, for example, block 442 in FIG. 10 and the above explanation thereof).

Additionally or alternatively to the first non-limiting embodiment, the reconfiguring means is adapted to cause reconfiguration of the first sensing configuration in response to finding that the first and second cardiac rates do not match and the second cardiac rate is not in an arrhythmia zone (as illustrated in the process flow of FIG. 10 leading to block 426).

Additionally or alternatively to the first non-limiting embodiment, the operational circuitry includes a rhythm analysis means for determining whether a treatable arrhythmia is taking place (see block 124 in FIG. 4), wherein the arrhythmia means is configured to modify a parameter of the rhythm analysis means in response to finding that the second cardiac rate is in an arrhythmia zone (for example block 442 in FIG. 10 as explained above).

Additionally or alternatively to the first non-limiting embodiment, the operational circuitry includes a therapy output circuit for delivering therapy to a patient (the device may include such a therapy circuit as explained above, such as by including a capacitor for therapy delivery linked to a DC:DC converter for generating high voltage therapy signal to store on the capacitor and an H-Bridge output circuit as is known in the art) and a charge confirmation means configured to determine that therapy is likely needed for the patient and to begin preparation for therapy delivery (see block 132 in FIG. 4), wherein the triggering means is further responsive to the charge confirmation means to cause the operational circuitry to use the second rate calculation means to generate a second cardiac rate and a confidence for use by the arrhythmia means and the reconfiguration means (as explained above with reference to block 132, the call to use the second rate calculation means can come at several stages of the cardiac signal analysis).

Additionally or alternatively to the first non-limiting embodiment, the plurality of sensing configurations include at least a first sensing configuration using a first sensing vector, and a second sensing configuration using a second sensing vector (FIG. 1 shows a system with multiple sense vectors available).

Additionally or alternatively to the first non-limiting embodiment, the input circuits comprise one or more filtering and one or more amplifying circuits (such inputs are descried above and may include analog or digital filtering circuits as well as an ECG Amplifier which may include one or more low noise amplifiers as are known in the art; features of amplification and filtering may be adjustable as discussed above).

Additionally or alternatively to the first non-limiting embodiment, the the second rate calculation means comprises: comparing means for comparing a first portion the patient's cardiac signal to a second portion of the patient's cardiac signal repeatedly at a plurality of lag depths that generate offsets of the first and second portions of the patients cardiac signal, wherein the first and second portions of the cardiac signal overlap with the second portion having a greater duration than the first portion to yield a plurality of comparison scores each corresponding to a lag depth; peak selector means to select a peak from the plurality of comparison scores the selected peak having a first lag depth; and confidence means to calculate a confidence associated with the selected peak. FIG. 7 shows a detailed example of such a method.

Additionally or alternatively the confidence means is configured to calculate a high confidence if the comparison score of the selected peak exceeds a threshold; and/or to calculate a high confidence if the plurality of comparison scores includes at least one peak at an integer multiple of the first lag depth; and/or to calculate a low confidence if all the comparison scores fail to exceed a threshold; and/or to calculate a low confidence if the selected peak fails to have at least one peak at an integer multiple of the first lag depth. Each of these options are discussed above relative to FIG. 7.

Additionally or alternatively to the first non-limiting embodiment, the device comprises a canister housing the operational circuitry and a lead or leads having one or more electrodes thereon and configured to couple to the canister to link the one or more electrodes to the operational circuitry electrically (as shown in FIG. 1 with canister 12 and lead 14).

Additionally or alternatively to the first non-limiting embodiment, the device may include storage means for storing cardiac signal data in response to the triggering means identifying a likely drop in signal quality of the first sensing configuration (as indicated in FIG. 10 at block 428).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes are available to the operational circuitry, the method comprising:
   the operational circuitry monitoring a first sensing configuration to determine whether an arrhythmia is occurring by the use of cardiac cycle detection to detect cardiac cycles and to calculate a first cardiac rate;
   the operational circuitry checking a signal quality of the first sensing configuration and identifying a likely drop in sensing quality of the first sensing configuration;
   in response to the likely drop in sensing quality of the first sensing configuration, the operational circuitry performing a rate analysis of the patient's cardiac signal using a method other than cardiac cycle detection to generate a second cardiac rate and a confidence; and either:
   the operational circuitry determining that an arrhythmia is occurring, based on at least the confidence of the rate analysis, and the operational circuitry initiating a therapy for the arrhythmia that is determined to be occurring; or
   the operational circuitry determining a drop in signal quality is occurring and the first sensing configuration should be changed, and the operational circuitry changing the first sensing configuration.

2. The method of claim 1 wherein the step of determining that an arrhythmia is occurring comprises identifying a type of arrhythmia using at least the confidence and the second cardiac rate.

3. The method of claim 1 wherein the step of checking a signal quality of the first sensing configuration is performed in response to determining that the first cardiac rate has exceeded a threshold.

4. The method of claim 1 wherein the step of performing a rate analysis of the patient's cardiac signal using a method other than cardiac cycle detection comprises:
   selecting a first portion the patient's cardiac signal to compare to a second portion of the patient's cardiac signal;
   repeatedly comparing the first portion of the patient's cardiac signal at a plurality of alignments defined by a plurality of corresponding lag depths to yield a plurality of comparison scores; and
   selecting one or more peak comparison scores and using a lag depth corresponding to the selected peak comparison scores to calculate the second cardiac rate.

5. The method of claim 4 wherein each of the first portion and second portion of the cardiac signal are obtained using the first sensing configuration.

6. The method of claim 4 wherein:
   the second portion of the cardiac signal at least partly overlaps the first portion of the cardiac signal;
   the first portion of the cardiac signal has a duration in the range of 500 milliseconds to 2000 milliseconds; and
   the second portion of the cardiac signal has a duration greater than that of the first portion of the cardiac signal.

7. The method of claim 4 wherein the step of selecting one or more peak comparison scores comprises defining a zero lag depth point, identifying a first peak comparison score having a first lag depth relative to the zero lag depth point, and determining that a second peak comparison score appears at a second lag depth relative to the zero lag depth point which is an integer multiple of the first lag depth.

8. The method of claim 1 further comprising the operational circuitry comparing the first cardiac rate to the second cardiac rate;
wherein the step of determining that an arrhythmia is occurring, rather than a drop in signal quality, based on a result of the rate analysis is performed in response to the operational circuitry finding that the second cardiac rate equals or exceeds the first cardiac rate; and
wherein the step of determining that the first sensing configuration should be changed is performed in response to the operational circuitry finding that the second cardiac rate is less than the first cardiac rate and below a threshold for declaration of tachyarrhythmia.

9. The method of claim 1 further comprising the operational circuitry comparing the first cardiac rate to the second cardiac rate and:
the step of determining that an arrhythmia is occurring, rather than a drop in signal quality, based on a result of the rate analysis is performed in response to finding that the second cardiac rate equals the first cardiac rate within predetermined bounds; and
the step of determining that the first sensing configuration should be changed is performed in response to finding that the second cardiac rate is different from the first cardiac rate outside the predetermined bounds.

10. A method of cardiac signal discrimination in an implantable cardiac device, the implantable medical device comprising a plurality of electrodes adapted for sensing cardiac signals of a patient and operational circuitry coupled to the plurality of electrodes such that a plurality of sensing configurations among the sensing electrodes are available to the operational circuitry, the method comprising:
the operational circuitry monitoring a first sensing configuration to determine whether an arrhythmia is occurring by the use of cardiac cycle detection to detect cardiac cycles and calculate a first cardiac rate;
the operational circuitry checking a signal quality of the first sensing configuration and identifying a likely drop in sensing quality of the first sensing configuration;
in response to the likely drop in sensing quality of the first sensing configuration, the operational circuitry performing a rate analysis of the patient's heart using a method other than cardiac cycle detection to yield a second cardiac rate;
the operational circuitry analyzing the second cardiac rate and determining that the second cardiac rate is in an arrhythmia zone; and
the operational circuitry determining that an arrhythmia is occurring, rather than a drop in signal quality, and the operational circuitry initiating a therapy for the arrhythmia that is determined to be occurring.

11. The method of claim 10 wherein the step of checking a signal quality of the first sensing configuration is performed by assessing signal quality of the first sensing configuration in an ongoing manner with each detected cardiac cycle.

12. The method of claim 10 wherein the step of checking a signal quality of the first sensing configuration is performed by assessing signal quality of the first sensing configuration at a predefined interval.

13. The method of claim 10 wherein the step of checking a signal quality of the first sensing configuration is performed by assessing signal quality of the first sensing configuration in response to determining that the cardiac rate of the patient, as assessed using cycle detection on the first sensing configuration, has exceeded a threshold.

14. The method of claim 10 wherein the step of performing a rate analysis of the patient's cardiac signal using a method other than cardiac cycle detection comprises:
selecting a first portion the patient's cardiac signal to compare to a second portion of the patient's cardiac signal;
repeatedly comparing the first portion of the patient's cardiac signal at a plurality of alignments defined by a plurality of corresponding lag depths to yield a plurality of comparison scores; and
selecting one or more peak comparison scores and using a lag depth corresponding to the selected peak comparison scores to calculate a cardiac rate.

15. An implantable medical device comprising:
a plurality of electrodes adapted for sensing cardiac signals of a patient; and
operational circuitry coupled to the plurality of electrodes such that a plurality of sensing configurations among the sensing electrodes are available to the operational circuitry; the operational circuitry configured to perform cardiac signal discrimination by:
the operational circuitry monitoring a first sensing configuration to determine whether an arrhythmia is occurring by the use of cardiac cycle detection to detect cardiac cycles and calculate a first cardiac rate;
the operational circuitry checking a signal quality of the first sensing configuration and identifying a likely drop in sensing quality of the first sensing configuration;
in response to the likely drop in sensing quality of the first sensing configuration, the operational circuitry performing a rate analysis of the patient's heart using a method other than cardiac cycle detection to yield a second cardiac rate;
the operational circuitry analyzing the second cardiac rate and determining that the second cardiac rate is in an arrhythmia zone; and
the operational circuitry determining that an arrhythmia is occurring, rather than a drop in signal quality, and the operational circuitry initiating a therapy for the arrhythmia that is determined to be occurring.

16. The device of claim 15 wherein the operational circuitry is configured such that checking a signal quality of the first sensing configuration is performed by assessing signal quality of the first sensing configuration in an ongoing manner with each detected cardiac cycle.

17. The device of claim 15 wherein the operational circuitry is configured such that checking a signal quality of the first sensing configuration is performed by assessing signal quality of the first sensing configuration at a predefined interval.

18. The device of claim 15 wherein the operational circuitry is configured such that checking a signal quality of the first sensing configuration is performed by assessing signal quality of the first sensing configuration in response to determining that the cardiac rate of the patient, as assessed using cycle detection on the first sensing configuration, has exceeded a threshold.

19. The device of claim 15 wherein the operational circuitry is configured such that performing a rate analysis of the patient's cardiac signal using a method other than cardiac cycle detection comprises:

the operational circuitry selecting a first portion the patient's cardiac signal to compare to a second portion of the patient's cardiac signal;

the operational circuitry repeatedly comparing the first portion of the patient's cardiac signal at a plurality of alignments defined by a plurality of corresponding lag depths to yield a plurality of comparison scores; and the operational circuitry selecting one or more peak comparison scores and using a lag depth corresponding to the selected peak comparison scores to calculate a cardiac rate.

* * * * *